(12) United States Patent
Zhou et al.

(10) Patent No.: US 11,844,866 B2
(45) Date of Patent: *Dec. 19, 2023

(54) GASTRORETENTIVE EXTENDED RELEASE DOSAGE FORM

(71) Applicant: Novelstar Pharmaceuticals, Inc., Cranbury, NJ (US)

(72) Inventors: Fang Zhou, Monroe Township, NJ (US); Shao Fu, Millstone, NJ (US)

(73) Assignee: NOVELSTAR PHARMACEUTICALS, INC., Cranbury, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/177,348

(22) Filed: Mar. 2, 2023

(65) Prior Publication Data

US 2023/0210780 A1    Jul. 6, 2023

Related U.S. Application Data

(63) Continuation of application No. 18/007,247, filed as application No. PCT/US2021/043405 on Jul. 28, 2021.

(60) Provisional application No. 63/057,673, filed on Jul. 28, 2020.

(51) Int. Cl.

| | |
|---|---|
| *A61K 9/20* | (2006.01) |
| *A61K 9/24* | (2006.01) |
| *A61K 31/4035* | (2006.01) |
| *A61K 31/519* | (2006.01) |
| *A61K 9/00* | (2006.01) |
| *A61K 47/14* | (2017.01) |
| *A61K 47/38* | (2006.01) |
| *A61K 47/44* | (2017.01) |

(52) U.S. Cl.
CPC ............ *A61K 9/209* (2013.01); *A61K 9/0065* (2013.01); *A61K 9/2013* (2013.01); *A61K 9/2031* (2013.01); *A61K 9/2054* (2013.01); *A61K 31/4035* (2013.01); *A61K 31/519* (2013.01); *A61K 47/14* (2013.01); *A61K 47/38* (2013.01); *A61K 47/44* (2013.01)

(58) Field of Classification Search
CPC . A61K 31/00; A61K 9/28; A61K 9/20; A61K 9/2004; A61K 9/2009; A61K 9/2013; A61K 9/2018; A61K 9/2022; A61K 9/2054; A61K 9/2059; A61K 9/2086; A61K 9/209
See application file for complete search history.

(56) References Cited

U.S. PATENT DOCUMENTS

| | | | |
|---|---|---|---|
| 8,470,367 B2 * | 6/2013 | Bhalachandra Dharmadhikari .... | A61K 9/2072 424/464 |
| 9,532,977 B2 | 1/2017 | Chen et al. | |
| 9,937,181 B2 | 4/2018 | Herbig et al. | |
| 2012/0141531 A1 | 6/2012 | Coulter et al. | |
| 2020/0155448 A1 | 5/2020 | Yan et al. | |

FOREIGN PATENT DOCUMENTS

| | | | | |
|---|---|---|---|---|
| WO | 2007002597 A2 | 1/2007 | | |
| WO | WO-2014174073 A1 * | 10/2014 | ........... | A61K 31/519 |
| WO | 2018232413 A1 | 12/2018 | | |
| WO | WO-2019073477 A1 * | 4/2019 | ......... | A61K 31/4035 |
| WO | 2020051585 A1 | 3/2020 | | |

\* cited by examiner

*Primary Examiner* — Micah Paul Young
(74) *Attorney, Agent, or Firm* — FOX ROTHSCHILD LLP

(57) ABSTRACT

A novel orally administrable dosage form including a drug/active layer for loading a therapeutic agent and an extension layer for retaining the API or drug dosage form in the stomach of a subject in need thereof. Also disclosed is a method of treating diseases with the dosage form.

27 Claims, 3 Drawing Sheets

GASTRORETENTIVE EXTENDED RELEASE DOSAGE FORM

CROSS-REFERENCE TO RELATED APPLICATIONS

This application claims the benefit of U.S. Provisional Patent Application No. 63/057,673, filed on Jul. 28, 2020, the content of which is incorporated by reference.

TECHNICAL FIELD

Disclosed herein is a novel orally administrable extended release dosage form which provides a safe and effective delivery of a therapeutic agent for the treatment of various PDE4 or TNF-α-associated diseases.

BACKGROUND

Pharmaceutical compounds that can inhibit PDE4 or TNF-α, may be beneficial therapeutics. Small-molecule inhibitors have demonstrated an ability to treat or prevent inflammatory diseases implicated by PDE4 or TNF-α. Apremilast is an inhibitor of phosphodiesterase 4 (PDE4) specific for cyclic adenosine monophosphate (cAMP). PDE4 inhibition results in increased intracellular cAMP levels and is effective in the inhibition of inflammatory mediator release.

Apremilast is (+) enantiomer of 2-[1-(3-ethoxy-4-methoxyphenyl)-2-methanesulfonylethyl]-4-acetylaminoisoindolin-1,3-dione having the following structure:

Compound I

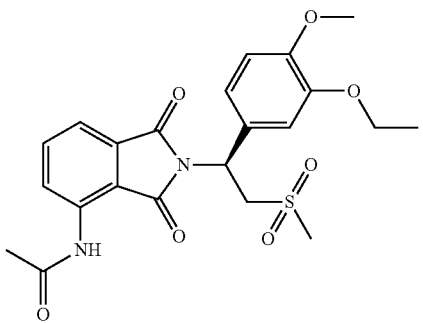

Apremilast may be prepared according to methods disclosed in U.S. Pat. Nos. 6,962,940; 7,208,516; 7,427,638; or 7,893,101, the entirety of each which is incorporated herein by reference.

Apremilast is a white to pale-yellow non hygroscopic powder, practically insoluble in aqueous buffers irrespective of pH range, soluble in acetone, acetonitrile, methylethylketone, methylene chloride and tetrahydrofuran. Active substance is classified as having low solubility and low permeability according to Biopharmaceutical Classification System (i.e. BCS Class 4).

Apremilast exhibits stereoisomerism due to presence of a single chiral center, with the (S)-enantiomer being pharmacologically active. Active substance stability studies and clinical studies have demonstrated that there is no interconversion of Apremilast (S)-enantiomer to its (R)-enantiomer both on storage and in vivo. Polymorphism has been observed for Apremilast and seven polymorphic forms (designated A-G) of the active substance were identified. The form B was found to be the most thermodynamically stable anhydrous form of Apremilast.

A need exists for extended release of apremilast in the stomach to provide safe and effective delivery of the therapeutic agent for the treatment of a variety of diseases.

SUMMARY

As set forth herein, the embodiments disclosed address the need. Various embodiments provide containing two or more layers for extended release of an active pharmaceutic ingredient. In contrast to previously reported dosage form where absorption of the active ingredient (e.g. Apremilast) takes place mainly (about 93%) in the proximal small bowel, the dosage form disclosed herein significantly improves the bioavailability of active ingredient by retaining the dosage form in the stomach of a subject for an extended period of time and releasing the therapeutic agent in a controlled manner.

An aspect of the patent document provides an orally administrable extended release dosage form comprising:
(a) an active pharmaceutical ingredient (API) layer comprising a first therapeutic agent, and one or more extended release agents providing extended release of the first therapeutic agent over a period of more than 8 hours through erosion in a medium, wherein the test medium comprises 900 ml of 50 mM pH 4.5 acetate buffer at 37° C. with sinker in a standard USP rotating paddle apparatus having a paddle rotating speed of 100 rpm;
(b) a retention layer comprising one or more excipients, wherein the one or more excipients are selected to achieve at least one of the following:
i. the dosage form stays afloat for more than 8 hours in the medium; and
ii. a length and a width in the retention layer of the dosage form both remain equal or greater than 10 mm for more than 8 hours in un-stirred deionized sitting water or in the medium.

In some embodiments, the dosage form further includes a third layer. In some embodiments, the third layer contains a second therapeutic agent. In some embodiments, the third layer keeps the dosage form afloat, wherein the API layer is sandwiched between the retention layer and the third layer.

In some embodiments, the first and second therapeutic agent is independently selected from tofacitinib and apremilast. In some embodiments, therapeutic agent is amorphous apremilast. In some embodiments, the first therapeutic agent is apremilast in an amount of about 60 mg in the dosage form.

In some embodiments, the one or more extended release agents in the first layer/API layer and the one or more excipients in the second/retention layer are selected to control the release of the first therapeutic agent in the medium such that (a) less than 30% of the first therapeutic agent is released within about 1 hour; and (b) from about 35% to about 80% of the first therapeutic agent is release within about 8 hours.

In some embodiments, more than 70% of the first therapeutic agent is released
in 16 hours.

In some embodiments, the one or more extended release agents in the API layer and the one or more floating agents in the retention layer are selected to control the release of the first therapeutic agent such that the dosage form administered once daily (QD) provides an area under curve (AUC) of the first therapeutic agent ranging from about 80% to about 125% of the AUC of the first therapeutic agent administered BID as an immediate release formulation.

In some embodiments, the one or more extended release agents in the API layer are selected from the group consisting of ethylcellulose, methylcellulose, hydroxypropyl cellulose, hypromellose, hypromellose phthalate, cellulose acetate, cellulose acetate phthalate, polyvinylalcohol, polyvinylacetate, polyacrylate, polymethacrylate, wax, and glyceryl ester of a fatty acid. In some embodiments, the one or more extended release agents in the drug layer comprises hypromellose with viscosity higher than 50 mPa·S (measured at 2% concentration in water at 20° C.) and glyceryl behenate. In some embodiments, the glyceryl behenate comprises glyceryl dibehenate in an amount of more than 50%, more than 60%, more than 70%, or more than 80% by weight in the glyceryl behenate. In some embodiments, the hypromellose and the glyceryl behenate are in a ratio ranging from about 1:10 to about 10:1. In some embodiments, the hypromellose and the glyceryl behenate independently range from about 5% to about 40% in the API layer. In some embodiments, the hypromellose has a viscosity of higher than 3000 mPa·S, wherein the hypromellose and the glyceryl behenate are in a ratio ranging from about 1:2 to about 2:1. and wherein the hypromellose and the glyceryl behenate independently range from about 5% to about 20% in the API/first layer.

In some embodiments, the one or more extended release agents comprise at least two hypromelloses, wherein one of the at least two hypromelloses has viscosity of higher than about 3,000 mPa·S and the other of the at least two hypromelloses has viscosity of lower than about 200 mPa·S.

In some embodiments, the ratio between the first therapeutic agent and the total amount of the one or more extended release agents ranges from about 1:1 to about 1:8. In some embodiments, the total weight of the one or more extended release agents ranges from about 10% to about 55% in the first layer. In some embodiments, the API/first layer and the retention/second layer are in a ratio ranging from about 1:4 to about 2:1.

In some embodiments, the API layer comprises a surfactant, preferably anionic or non-ionic with an HLB (hydrophilic lipophilic balance) value greater than 10.0, for example greater than 15.0 and more particularly greater than 20.0. Suitable anionic surfactants include alkyl sulfates, alkyl sulfonates, alkyl phosphates, alkyl carboxylates and docusate. A preferred anionic surfactant is sodium lauryl sulfate. Preferred nonionic surfactants include ethoxylates, fatty acids esters of polyhydroxy compounds, fatty acid esters of glycerol, and fatty acid esters of sorbitol. One example is Poloxamer, which is a series of closely related block copolymers of ethylene oxide and propylene oxide conforming to the general formula $HO(C2H4O)_a(C3H6O)_b(C2H4O)_aH$. In some embodiments, the ratio between the first therapeutic agent and the total amount of surfactant ranges from about 10:1 to about 1:4. In some embodiments, the ratio is 9:1, 8:1, 6:1, 4:1, 2:1, 1:1, or 1:2.

In some embodiments, the one or more excipients in the retention layer comprise low density agents selected from the group consisting of cellulose acetate, hydrogenated vegetable oil, glyceryl behenate, ethylcellulose, and wax. In some embodiments, the one or more excipients in the retention/second layer comprise one or more swelling agent selected from the group consisting of hypromellose, hydroxypropyl cellulose, polyethylene oxide, carboxymethylcellulose, croscarmellose sodium, sodium starch glycolate, cross-linked povidone, and chitosan.

In some embodiments, the one or more excipients in the retention/second layer comprise polyethylene oxide having MW of no less than 1000 kDa and cellulose acetate in a ratio ranging from about 10:1 to about 1:1. In some embodiments, the one or more excipients in the retention/second layer comprise polyethylene oxide having MW of no less than 1000 kDa and cellulose acetate independently range from about 5% to about 60% in the retention layer. In some embodiments, the polyethylene oxide and the cellulose acetate are in a ratio ranging from about 5:1 to about 2:1.

The dosage form further includes a low viscosity hypromellose in an amount ranging from about 5% to about 50% in the retention/second layer, wherein the low viscosity hypromellose has a viscosity of less than 150 mPa·S.

In some embodiments, the retention layer further comprises an effervescent agent and an acid source, wherein the total weight of the effervescent agent and the acid source ranges from about 5% to about 20% in the retention layer. In some embodiments, the one or more extended release agents in the API layer and the one or more excipients in the retention layer are selected to control retention of the dosage form in the stomach such that the dosage form begins to float in less than 30 minutes in the medium.

In some embodiments, the one or more excipients in the retention layer are selected such that the length and the width of the retention layer independently expand from about 10% to about 20% in the medium within about 30 minutes. In some embodiments, the one or more excipients in the retention layer are selected such that the length and the width of the retention layer independently expands from about 30% to about 50% in the medium within about 8 hours. In some embodiments, the length exceeds 18 mm and the width exceeds 10 mm within 30 minutes in the medium. The length and width of the retention layer ensures that the dosage form is retained in the stomach for a desirable period of time. The length and width of the retention layer defines a plane substantially parallel to the API layer.

In some embodiments, the therapeutic agent, the pharmaceutically acceptable salt, amorphous, polymorph, solvate or hydrate thereof ranges from about 30 to about 100 mg in the dosage form. In some embodiments, the ratio between the therapeutic agent and the total amount of the one or more extended release agents ranges from about 2:1 to about 1:4. In some embodiments, the total weight of the one or more extended release agents ranges from about 10% to about 55% in the API layer. In some embodiments, the retention layer comprises one or more swelling agents and the total weight of the one or more one or more swelling agents ranges from about 25% to about 80%. In some embodiments, the retention layer further comprises an effervescent agent and an acid source, wherein the total weight of the effervescent agent and the acid source ranges from about 5% to about 20% in the retention layer.

Another aspect provides a method of treating a disease in a subject, comprising administering to the subject the dosage form described herein, wherein the disease is selected from the group consisting of psoriasis, ankylosing spondylitis, Behcet's disease, rheumatoid arthritis, atopic dermatitis, Crohn's disease, ulcerative colitis.

In some embodiments, the dosage form is administered once daily. In some embodiments, a total daily amount of about 60 mg of apremilast or equivalent amount of the pharmaceutically acceptable salts, amorphous, polymorph, solvate or hydrate thereof is administered to the subject.

In some embodiments, the method further includes administering to the subject an additional agent selected from the group consisting of anti-inflammatories (e.g.

NSAIDs), immunosuppressants, topical corticosteroids, calcineurin inhibitors, Cox-2 inhibitors, TNF-alpha inhibitors, antirheumatics, antipsoriatics, interleukin inhibitors, narcotic analgesic combinations, salicylates, glucocorticoids and topical rubefacients.

A method of providing in a subject an area under curve (AUC in a 24 hour period or 0 to infinity) of a first therapeutic agent ranging from about 70% to about 125% of the AUC of the first therapeutic agent orally administered twice a day (BID) as an immediate release formulation. The method includes administering orally to the subject once a day the dosage form of claim 1, wherein the amount of the first therapeutic agent in the dosage form ranges from about 60% to about 150% of the daily total amount of the first therapeutic agent in the immediate release formulation.

DETAILED DESCRIPTION

Figure 1:
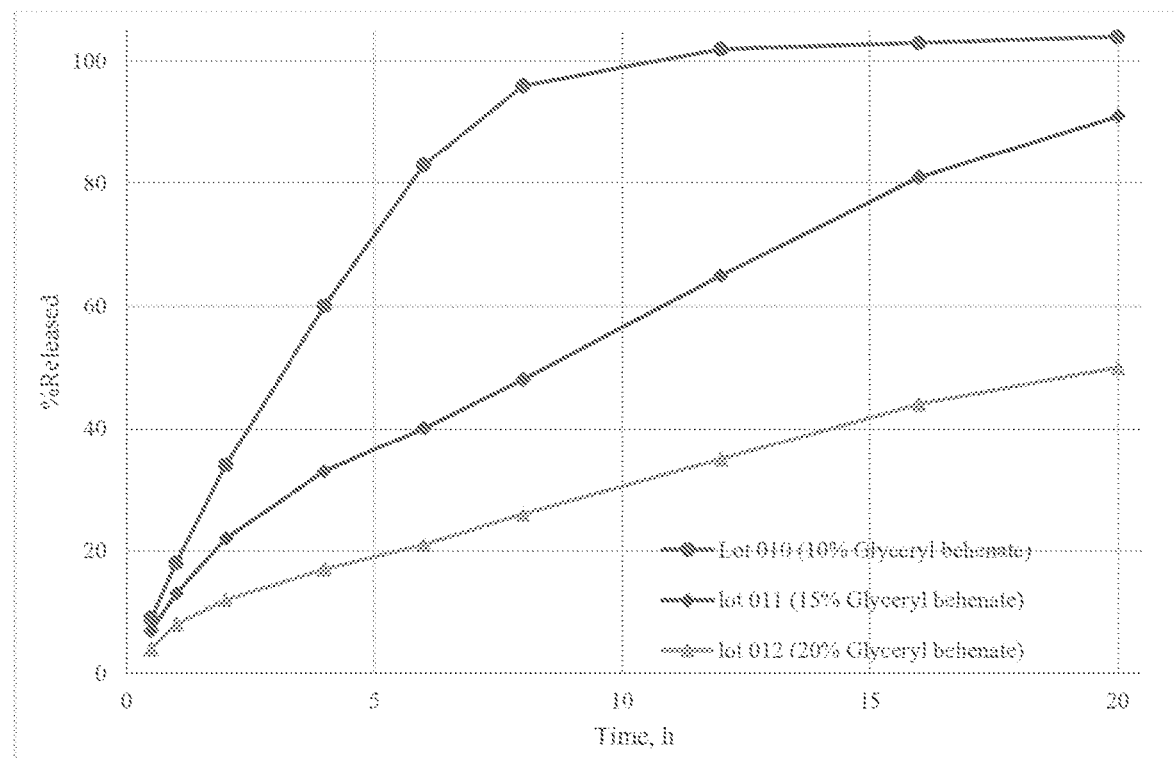
FIG. 1 shows the effect of glyceryl behenate in different concentrations on drug release for different apremilast ER tablets in pH 4.5, 50 mM Acetate buffer with 2% Tween 80 by Paddle, 75 rpm.

Various embodiments of this patent document disclose an orally administrable dosage form of a therapeutic agent or an active pharmaceutical ingredient (API). The dosage form includes multiple layers and provides a suitable retention time for the compound to be released in the stomach and absorbed in the upper gastrointestinal tract of a patient. Further, the pharmacokinetics of the compound in an extend release form ensures a desirable therapeutic profile and promotes patient compliance.

While the forgoing text may reference or exemplify specific embodiments of a dosage form or a method of treating a disease or condition, it is not intended to limit the scope of the dosage or method to such particular reference or examples. Various modifications may be made by those skilled in the art, in view of practical and economic considerations, such as the amount and ratio of different excipients in the dosage form.

As used herein, the articles "a" and "an" refer to "one or more" or "at least one," unless otherwise indicated. That is, reference to any element or component of an embodiment by the indefinite article "a" or "an" does not exclude the possibility that more than one element or component is present.

As used herein, the term "about" generally refers to plus or minus 10% of the indicated number. For example, "about 10%" may indicate a range of 9% to 11%, and "about 20" may mean from 18 to 22. Other meanings of "about" may be apparent from the context, such as rounding off, so, for example "about 1" may also mean from 0.5 to 1.4. As used herein, the term "and/or" includes any and all combinations of one or more of the associated listed items.

The term "AUC" refers to the area under the plasma concentration-time curve. When comparing a tested dosage form with a reference, the same timeframe for the tested form and the reference are used. In some embodiments, the timeframe encompasses time 0 to infinity. In some embodiments, the timeframe is the 24-hour period after administration (time point 0) of the dosage form.

The term "subject" as used herein is intended to include human and non-human animals. Non-human animals include all vertebrates, e.g. mammals and non-mammals, such as non-human primates, sheep, dogs, cats, cows, horses, chickens, amphibians, and reptiles, although mammals are preferred, such as non-human primates, sheep, dogs, cats, cows and horses. Preferred subjects include human patients in need of enhancement of an immune response. The methods are particularly suitable for treating human patients having a disorder that can be treated by augmenting the immune response.

The term "therapeutic agent" as used herein refers to a compound or agent having a therapeutic effect for treating a disease.

"Treating" or "treatment of a disease state includes: 1) preventing the disease state, i.e. causing the clinical symptoms of the disease state not to develop in a subject that may be exposed to or predisposed to the disease state, but does not yet experience or display symptoms of the disease state; 2) inhibiting the disease state, i.e., arresting the development of the disease state or its clinical symptoms; 3) or relieving the disease state, i.e., causing temporary or permanent regression of the disease state or its clinical symptoms.

The term "effective amount" as used herein means that amount of a formulation or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. Specific doses can be readily determined by one having ordinary skill in the art, using routine procedures.

The term "pharmaceutically acceptable carrier" as used herein includes any and all solvents, dispersion media, coatings, excipients, and the like that are physiologically compatible. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, penetration enhancers, emulsifiers, thickeners, emollients, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences.

A "pharmaceutically acceptable salt" refers to a salt of the active ingredient. The salt form retains the desired biological activity of the parent compound and does not impart any undesired toxicological effects. The pharmaceutically acceptable salt may be an inorganic acid salt, an organic acid salt, or a metal salt.

The term "extended release" (ER) as used herein is defined as release of an active pharmaceutical ingredient over an extended period of time, which is greater than about 2 hour, preferably greater than about 4 hour, more preferably greater than about 8 hour, more preferably greater than about 12 hour, more preferably greater than about 16 hour, or up to more than about 24 hour.

The term "immediate release" as used herein refers to release of an active pharmaceutical ingredient more than or equal to about 80% in less than or equal to about 1 hour. Typically, the release of the active pharmaceutical ingredient in an immediate release formulation is more than or equal to about 80% in less than or equal to about 30 minutes.

The term "release" or "released", when used in connection with a pharmaceutical composition or dosage form, refers to the portion of the drug substance that leaves the dosage form following contact with an aqueous environment. Unless otherwise indicated, the quantity of drug released from a dosage form is measured by dissolution testing in aqueous medium as described in this invention. The results of the dissolution testing are reported as % (w/w) released as a function of time or as the release time.

An aspect of this patent document provides a multi-layered orally administrable dosage form. The dosage form includes
(a) an API layer comprising a first therapeutic agent and one or more extended release agents providing extended release of the first therapeutic agent over a period of more than 8 hours, more than 10 hours, more than 15 hours, or more than 20 hours through erosion in a medium, wherein the test medium comprises 900 ml of 50 mM pH 4.5 acetate buffer at 37° C. with sinker in a standard USP rotating paddle apparatus having a paddle rotating speed of 100 rpm, and the medium may contain 2% Tween 80 (polysorbate 80, polyoxyethylene sorbitan monooleate);
(b) a retention layer comprising one or more excipients, wherein the one or more excipients are selected to achieve at least one of the following:
  i. the dosage form stays afloat for more than 5 hours, more than 8 hours, more than 12 hours, more than 16 hours, more than 20 hours, or more than 24 hours in the medium; and
  ii. a length and a width in the retention layer of the dosage form both remain equal or greater than 10 mm for more than 5 hours, more than 8 hours, more than 12 hours, more than 16 hours, or more than 20 hours in un-stirred deionized sitting water or in the medium of (a).

The dosage form may contain two, three or more layers. Two or more therapeutic agents can be included in the dosage form. For instance, the dosage form may include a third layer containing a second therapeutic agent, which is in immediate release form or an extended release form and can be same or different from the first therapeutic agent. Alternatively, the dosage form may include a third layer for keeping the dosage form retention or afloat, wherein the API layer is sandwiched between the two retention layers. In some embodiments, the dosage form is a two-layer tablet. The API layer and the retention layer are in a ratio of 1:4, 1:3, 1:2, 1:1, or 2:1.

The two layers are compressed against each other and remain attached during the absorption of the active ingredient in the stomach. The retention layer serves as a retention layer and/or floating layer and keeps the dosage form retained or suspended in stomach so that the absorptance of the active ingredient takes place mainly in the upper gastrointestinal tract. The retention layer can contain low density and/or suitable materials (e.g. swelling component) so that the dosage form stays afloat or the size of dosage form remains bigger than the pyloric diameter of the stomach to extend the retention time and prolong the absorption of the therapeutic agent or the active ingredient. More than 95%, more than 90%, more than 80%, more than 70%, more than 60%, or more than 50% of the therapeutic agent of the dosage form is released and absorbed in the upper gastrointestinal tract.

The dosage form can be a tablet, which may vary in shape including, but not limited to oval, triangle, almond, peanut, parallelogram, pentagonal. The final dosage form may also be coated with suitable coating materials for either functional or non-functional use known to those skilled in the art of formulation development without hindering the release of therapeutic agent from the gastro retentive dosage form.

The ratio between the API layer containing the active ingredient and the retention layer containing the retention and/floating agent may vary depending on the specific composition of each layer. The ratio generally ranges from about 5:1 to about 1:5, from about 4:1 to about 1:4, from about 3:1 to about 1:3, from about 2:1 to about 1:2, from about 3:1 to about 1:1, from about 2:1 to about 1:1, from about 1:1 to about 1:2, or from about 1:1 to about 1:3.

The amount of the therapeutic agent, its pharmaceutically acceptable salt, amorphous, polymorph, solvate or hydrate thereof in the dosage form may vary. In some embodiments, the compound ranges from about 1 mg to about 120 mg, from about 10 mg to about 100 mg, from about 20 mg to about 80 mg, from about 30 mg to about 80 mg, from about 40 mg to about 80 mg, from about 40 mg to about 70 mg, from about 50 mg to about 70 mg, from about 55 mg to about 65 mg. In some more examples, the amount of API or equivalent amount of the pharmaceutically acceptable amorphous, polymorph, solvate or hydrate thereof is about 10, about 20, about 30, about 40, about 50, about 55, about 60, about 65, or about 70 mg, about 80, about 90, about 100 mg or about 120 mg. In some embodiments, the first therapeutic agent is amorphous apremilast in an amount of about 50, about 55, about 60, about 65, or about 70 mg, or about 80 mg, or about 120 mg in the dosage form. In some embodiments, the first therapeutic agent is amorphous apremilast.

The dosage form of this patent document releases the active agent having an absorption window in the upper part of the gastrointestinal tract in a controlled manner for improved absorption and efficacy compared to immediate release dosage forms or non-gastroretentive extended release dosage form. An extended release dosage form according to this patent document is one that achieves slow release of a drug over an extended period of time, thereby extending the duration of drug action over that achieved by conventional delivery.

The dosage for the therapeutic agent (QD administration) ranges from about 20 to about 150 mg. In some embodiments, the QD dosage is 30 mg, 40 mg, 50 mg, 60 mg, 70 mg, 80 mg, 90 mg, 100 mg, or 120 mg. In some embodiments, the therapeutic agent has the highest solubility in stomach of the subject relative to other locations of gastrointestinal path. The therapeutic agent is selected from the group consisting of tofacitinib, apremilast, pharmaceutically acceptable salt thereof, and stereoisomers thereof. In some embodiments, the therapeutic agent is amorphous apremilast.

The release of the therapeutic agent can be determined in a medium comprising 900 ml of 50 mM pH 6.8 or 4.5 phosphate buffer with 2% Tween 80 at 37° C. with sinker in a standard USP rotating paddle apparatus having a paddle rotating speed of 100 rpm. Under this condition, in some embodiments of any dosage form or method disclosed herein, one, two or three of any of the following release can be achieved:

(a) less than 10%, less than 15%, less than 20%, less than 25%, less than 30%, or less than 35% of the therapeutic agent is released within about 1 hour; or from about 3% to about 20%, from about 5% to about 15%, from about 5% to about 10%, or from 8% to about 12% of the therapeutic agent is released by the time point of the first hour;

(b) from about 25% to about 90%, from about 30% to about 85%, from about 35% to about 70%, from about 40% to about 70%, from about 50% to about 60%, from about 35% to about 50%, from about 40% to about 60%, from about 50% to about 80%, from about 60% to about 80%, from about 65% to about 75% or from about 35% to about 80% of the therapeutic agent is release within about 8 hours or by the time point of the $8^{th}$ hour; and/or (c) more than 60%, more than 70%, more than 80%, more than 90%, or more than 95% of the therapeutic agent is released in 16 hours or by the time point of the $16^{th}$ hour.

In some embodiments of any dosage form or method disclosed herein, one, two or three of any of the above release can be achieved in a medium comprising 900 ml of 50 mM pH 4.5 acetate buffer with 2% Tween 80 at 37° C. with sinker in a standard USP rotating paddle apparatus having a paddle rotating speed of 100 rpm. In some embodiments of any dosage form or method disclosed herein, one, two or three of any of the above release can be achieved in a medium comprising 900 ml of 0.1N HCl with 2% Tween 80 at 37° C. with sinker in a standard USP rotating paddle apparatus having a paddle rotating speed of 100 rpm.

In some embodiments, the API layer is substantially eroded away by the time all the API has been released. In some embodiments, the release of the API is controlled by a matrix erosion mechanism.

In some embodiments of any dosage form or method disclosed herein, the following absorptions in human can be achieved when the dosage form is administered once daily to the subject. In some embodiments, the dosage form is administered with food.

(a) an area under curve (AUC) ranging from about 60% to about 140%, from about 70% to about 130%, from about 80% to about 125%, from about 80% to about 120%, from about 85% to about 115%, from about 90% to about 100% or from about 90% to about 110% of the AUC of the same therapeutic agent with the same daily dose administered BID in an immediate release formulation (reference); non-limiting examples of the percentages of the AUC of the dosage form over the AUC of the reference include about 70%, about 75%, about 80%, about 85%, about 90%, about 95%, about 100%, about 105%, about 110%, about 115%, and about 120%; in some embodiments, the AUC is $AUC_{0-\infty}$; in some embodiments, the AUC is $AUC_{0-24}$. and/or (b) a ratio of geometric mean plasma Cmax to Cmin ranging from about 5:1 to about 100:1, from about 10:1 to about 100:1, from about 10:1 to about 90:1, from about 10:1 to about 80:1, from about 10:1 to about 60:1, from about 10:1 to about 50:1, from about 10:1 to about 40:1, from about 10:1 to about 30:1, from about 10:1 to about 20:1, from about 5:1 to about 50:1, or from about 5:1 to about 20:1; and/or (c) $C_{max}$ ranging from about 70% to about 150%, from about 80% to about 130%, from about 80% to about 125;%, from about 80% to about 120%, from about 85% to about 115%, from about 90% to about 100% or from about 90% to about 110% of the $C_{max}$ of the same therapeutic agent with the same daily dose administered BID in an immediate release formulation (reference); non-limiting examples of the percentages of the $C_{max}$ of the dosage form over the $C_{max}$ of the reference include about 70%, about 75%, about 80%, about 85%, about 90%, about 95%, about 100%, about 105%, about 110%, about 115%, about 120%, and about 130%.

In some embodiments of any dosage form or method disclosed herein for API absorption in human, the one or more extended release agents in the API layer and the one or more floating agents in the retention layer are selected to control the release of the first therapeutic agent ranging from about 40 mg to about 80 mg such that the dosage form administered QD provides an area under curve (AUC) of the first therapeutic agent ranging from about 80% to about 125% of the AUC of the first therapeutic agent in a daily amount of about 60 mg administered BID as an immediate release formulation. In some embodiments, the first therapeutic agent is apremilast.

In some embodiments of any dosage form or method disclosed herein, the dosage form disclosed herein contains about 30 mg, about 40 mg, about 50 mg, about 60 mg, about 70 mg, about 80 mg, about 100 mg or about 120 mg apremilast.

In some embodiments of absorption in human, the one or more extended release agents in the API layer and the one or more excipients in the retention layer are selected to control the release of the first therapeutic agent ranging from about 8 mg to about 15 mg, about 15 mg to about 25 mg, about 20 mg to about 30 mg such that the dosage form administered once daily (QD) provides an area under curve ($AUC_{0-\infty}$) of the first therapeutic agent ranging from about 80% to about 125% of the AUC of the first therapeutic agent in a daily dosage of about 10, about 20 or about 25 mg administered BID as an immediate release formulation, wherein the first therapeutic agent is tofacitinib.

Extended release agents suitable for the dosage form include excipients well known in the pharmaceutical art for their release retarding properties. Examples of such agents include, but are not limited to, polymeric release retardants, non-polymeric release retardants or any combinations thereof.

Polymeric extended release agents employed for the purpose of this patent document include, but are not limited to, cellulose derivatives; polyhydric alcohols; saccharides, gums and derivatives thereof; vinyl derivatives, polymers, copolymers or mixtures thereof; maleic acid copolymers; polyalkylene oxides or copolymers thereof; acrylic acid polymers and acrylic acid derivatives; or any combinations thereof. Cellulose derivatives include, but are not limited to, ethyl cellulose, methylcellulose, hydroxypropylmethylcellulose (hypromellose), hydroxypropyl cellulose (HPC), hydroxyethyl cellulose, hydroxymethyl cellulose, hydroxyethyl methyl cellulose, carboxymethyl cellulose (CMC), or combinations thereof. Polyhydric alcohols include, but are not limited to, polyethylene glycol (PEG) or polypropylene glycol; or any combinations thereof. Saccharides, gums and their derivatives include, but are not limited to, dextrin, polydextrin, dextran, pectin and pectin derivatives, alginic acid, sodium alginate, starch, hydroxypropyl starch, guar gum, locust bean gum, xanthan gum, karaya gum, tragacanth, carrageenan, acacia gum, arabic gum, fenugreek fibers or gellan gum or the like; or any combinations thereof. Vinyl derivatives, polymers, copolymers or mixtures thereof include, but are not limited to, polyvinyl acetate, polyvinyl alcohol, mixture of polyvinyl acetate (8 parts w/w) and polyvinylpyrrolidone (2 parts w/w) (Kollidon SR), copolymers of vinyl pyrrolidone, vinyl acetate copolymers, polyvinylpyrrolidone (PVP); or combinations thereof. Polyalkylene oxides or copolymers thereof include, but are not limited to, polyethylene oxide, polypropylene oxide, poly (oxyethylene)-poly (oxypropylene) block copolymers (poloxamers) or combinations thereof. Maleic acid copolymers include, but are not limited to, vinylacetate maleic acid anhydride copolymer, butyl acrylate styrene maleic acid anhydride copolymer or the like or any combinations thereof. Acrylic acid polymers and acrylic acid derivatives include, but are not limited to, carbomers, methacrylic acids, polymethacrylic acids, polyacrylates, polymethacrylates or the like or combinations thereof Polymethacrylates, include, but are not limited to, a) copolymer formed from monomers selected from methacrylic acid, methacrylic acid esters, acrylic acid and acrylic acid esters c) copolymer formed from monomers selected from ethyl acrylate, methyl methacrylate and trimethylammonioethyl methacrylate chloride, or the like or any combinations thereof.

Non-polymeric extended release agents include, but are not limited to, fats, oils, waxes, fatty acids, fatty acid esters, long chain monohydric alcohols and their esters or combinations thereof. In an embodiment, non-polymeric release retardants employed in the present invention, include, but are not limited to, Cutina (hydrogenated castor oil), Hydrobase (hydrogenated soybean oil), Castorwax (hydrogenated castor oil), Croduret (hydrogenated castor oil), Carbowax, Compritol (glyceryl behenate), Sterotex (hydrogenated cottonseed oil), Lubritab (hydrogenated cottonseed oil), Apifil (wax yellow), Akofine (hydrogenated cottonseed oil), Softtisan (hydrogenated palm oil), Hydrocote (hydrogenated soybean oil), Corona (lanolin), Gelucire (macrogolglycerides lauriques), Precirol (glyceryl palmitostearate), Emulcire (cetyl alcohol), Plurol diisostearique (polyglyceryl diisostearate), and Geleol (glyceryl stearate), and mixtures thereof.

The amount of extended release agents relative to the active agent may vary depending on the release rate desired, nature of the retardants and their physicochemical characteristics. The amount of the release retardant in the API layer of the dosage form generally varies from about 5% to about 60% by weight of the composition. Preferably, the amount of release retardant varies from about 5% to about 50% by weight of the API layer of the dosage form.

The dosage form may contain 1, 2, 3 or more different extended release agents. The ratio between the active ingredient and each individual extended release agent by weight ranges from about 4:1 to about 1:5, from about 3:1 to about 1:4, from about 2:1 to about 1:3, from about 3:2 to about 4:3, from about 2:1 to about 3:4, from about 2:1 to about 1:3, from about 1:1 to about 1:8, from about 1:1 to about 1:5, from about 1:1 to about 1:3, from about 1:1 to about 1:2, or from about 1:2 to about 1:3. In exemplary embodiments, the ratio between the active ingredient and each individual extended release agent by weight is about 3:1, about 2:1, about 3:2, about 1:1, about 1:2, about 2:3, or about 1:3. In some embodiments, the total amount of the 1, 2, 3 or more extended release agents ranges from about 5% to about 95%, from about 5% to about 80%, from about 5% to about 70%, from about 5% to about 60%, from about 5% to about 50%, from about 10% to about 80%, from about 15% to about 70%, from about 10% to about 60%, from about 10% to about 50%, from about 5% to about 40%, from about 10% to about 30%, from about 10% to about 25%, or from about 5% to about 20% by weight in the API layer. In some embodiments, each individual extended release agent ranges from about 5% to about 95%, from about 5% to about 80%, from about 5% to about 70%, from about 5% to about 60%, from about 5% to about 50%, from about 10% to about 80%, from about 15% to about 70%, from about 10% to about 60%, from about 10% to about 50%, from about 5% to about 40%, from about 10% to about 30%, from about 10% to about 25%, or from about 5% to about 20% by weight in the API layer. In some embodiments, the extended release agents are selected from 1, 2 or 3 of ethylcellulose, methylcellulose, hydroxypropyl cellulose, hypromellose, hypromellose phthalate, cellulose acetate, cellulose acetate phthalate, polyvinylalcohol, polyvinylacetate, polyacrylate, polymethacrylate, glyceryl behenate, hydrogenated vegetable oil, wax, and glyceryl ester of a fatty acid (glyceride). Wax includes synthetic wax, microcrystalline wax, paraffin wax, Carnauba wax, beeswax or a mixture thereof. Nonlimiting examples of glyceride include glyceryl monooleate, glyceryl monostearate, glyceryl palmitostearate, polyethoxylated castor oil derivatives, hydrogenated vegetable oils, glyceryl behenate, glyceryl tristearate, glyceryl tripalmitate or a mixture thereof.

In some embodiments, the extended release agents in the API layer include hydroxypropyl methylcellulose (hypromellose), hydroxypropyl cellulose, and glyceryl behenate. In some embodiments, the extended release agents include at least two hypromelloses, wherein one of the at least two hypromelloses has viscosity of higher than 3,000 mPa·S (e.g. 3200, 3500, 3800, 4000, 4500, or 5000 mPa·S) and the other of the at least two hypromelloses has viscosity of lower than about 200 mPa·S (e.g. 180, 150, 100, 80, 50 or 3 mPa·S). In some embodiments, the ratio of the high viscosity and low viscosity hypromelloses is about 20:1, 15:1, 10:1, 8:1, 6:1, 4:1, 2:1, 1:1, 1:2, 1:4, 1:6, 1:8, 1:10, 1:15, or 1:20.

In some embodiments, the extended release agents include hypromellose and glyceryl ester of a fatty acid. In some embodiments, the hypromellose has a viscosity of higher than 50, higher than 100, higher than 200, higher than 500, higher than 1,000, higher than 2,000, or higher than 3,000 mPa·S. In some embodiments, the hypromellose has a viscosity of higher than 3,000 mPa·S (e.g. 4000, 5000, 15,000, or 100,000 mPa·S) The glyceryl ester can include one, two or three of mono-glyceryl ester, di-glyceryl ester, and tri-glyceryl ester of the fatty acid. The fatty acid can be saturated or unsaturated. Examples of saturated fatty acid include Caprylic acid, Capric acid, Lauric acid, Stearic acid, Arachidic acid, Behenic acid, Lignoceric acid, Cerotic acid. Examples of unsaturated fatty acid include Myristoleic acid, Palmitoleic acid, Sapienic acid, Oleic acid, Elaidic acid, Vaccenic acid, and Linoleic acid.

The hypromellose and the glyceryl ester of the fatty acid may independently range from about 5% to about 50%, from about 5% to about 30%, from about 10% to about 20% or from about 15% to about 20% in the API layer. In some embodiments, the glyceryl ester of the fatty acid has a hydrophilic-lipophilic balance (HLB) value of about 1, about 1.5, about 2, about 2.5 or about 3. HLB value can be readily calculated by well known Griffin equation. In some embodiments, the fatty acid is behenic acid and the glyceryl ester (glyceryl behenate) is a mixture of monoglyceride, diglycerides and triglycerides of behenic acid. In some embodiments, the glyceryl behenate has an HLB value of 2. In some embodiments, the glyceryl behenate contains more than 50%, more than 60% or more than 70% of diglycerides of behenic acid and less than 30%, less than 20%, or less than 15% of monoglycerides of behenic acid.

In some embodiments, the hypromellose and the glyceryl behenate are in a ratio ranging from about 1:10 to about 10:1. Exemplary ratios between the hypromellose and the glyceryl behenate include 10:1, 8:1, 6:1, 4:1, 3:1, 2:1, 1:1, 1:2, 1:3, 1:4, 1:6, 1:8, and 1:10. In some embodiment, the hypromellose and the glyceryl behenate are independently in the amount of about 5%, about 10%, about 15%, about 20%, or about 25%, or about 30%, about 35%, or about 40% in the API layer.

The dosage form of this patent document may contain gas generating agents. For instance, an acid source as effervescent couples may aid in the formation of porous preferably honeycombed structure that enhances the buoyancy of the dosage form. Gas generating agents that may be used herein include, but are not limited to, sodium bicarbonate, sodium glycine carbonate, potassium bicarbonate, ammonium bicarbonate, sodium bisulfite, sodium metabisulfite, and the like. The gas generating agent interacts with an acid source triggered by contact with water or simply with gastric acid to generate carbon dioxide or sulphur dioxide that gets entrapped to form highly porous matrix and improve the floating characteristics. An acid may be added, including, but not limited to, citric acid and maleic add. In one embodiment the gas generating agent is sodium bicarbonate and the acid source is citric acid. In some embodiments, the gas generating agent in the retention layer or in an additional layer other than the API layer ranges from about 1% to about 30%, from about 1% to about 20%, from about 1% to about 10%, from about 1% to about 8% in the retention layer, from about 3% to about 10% or from about 3% to about 15%, wherein the ratio between the gas generating agent and the acid source ranges from about 1:5 to about 5:1, from about 4:1 to about 1:4, from about 3:1 to about 1:3, from about 2:1 to about 1:2, from about 3:1 to about 1:1, from about 2:1 to about 1:1, from about 1:1 to about 1:2, or from about 1:1 to about 1:3.

Materials that can lower the density of the dosage form can also be incorporated. In some embodiments, the retention layer for tablet retention/floating comprises one or more low density excipients selected from the group consisting of cellulose acetate, hydrogenated vegetable oil, glyceryl behenate, ethylcellulose and combinations thereof. In some embodiments, the weight ratio for the one or more low density excipients are adjusted such that the density of the gastroretentive dosage form is lower than the density of the gastric fluid in a subject.

Swelling and expansion is a potentially reliable retention mechanism wherein on swallowing the dosage form swells to an extent that not only decreases the density of the dosage form but also prevents exit from the stomach through the pylorus. As a result, the dosage form is retained in the stomach for a long period of time. These dosage forms are excluded from the passage of the pyloric sphincter as they exceed a diameter of approximately 10-12 mm in their swollen or expanded state. Besides poly (ethylene oxide) and hydroxyalkyl alkylcellulose (e.g., hydroxypropyl methyl cellulose), additional materials include fenugreek fibers and gums of natural origin like locust bean gum as disclosed in U.S. patent Ser. No. 10/463,623, which is incorporated by reference. In some embodiments, the retention/second layer or an additional layer other than the API/first layer contains 1, 2, 3, or more swelling agents, the total weight of which ranges from about 5% to about 95%, from about 10% to about 80%, from about 15% to about 70%, from about 25% to about 75%, from about 35% to about 75%, from about 45% to about 75%, from about 55% to about 75%, from about 65% to about 75%, from about 10% to about 50%, from about 5% to about 40%, from about 10% to about 30%, from about 10% to about 25%, or from about 5% to about 20% by weight in the retention layer or the additional layer. In some embodiments, the retention layer or an additional layer other than the API layer contains 1, 2, 3, or more swelling agents, wherein an individual swelling agent may range from about 5% to about 95%, from about 10% to about 80%, from about 15% to about 70%, from about 25% to about 75%, from about 35% to about 75%, from about 35% to about 55%, from about 35% to about 50%, from about 65% to about 75%, from about 10% to about 50%, from about 5% to about 40%, from about 10% to about 30%, from about 10% to about 25%, or from about 5% to about 20% by weight in the floating/retention layer or the additional layer. In some embodiments, the retention layer or the additional layer contains 1, 2, 3 of swelling agent selected from Polyethylene oxide (Polyox WSR 303 LEO), Hypromellose (Pharmacoat 603), and Hypromellose (Methocel K100M Premium CR).

In some embodiments, the retention layer includes one or more agent selected from polyethylene oxide (PEO), cellulose acetate, hydroxyalkyl alkylcellulose (e.g., hypromellose, hydroxypropyl cellulose), and any combination thereof. In some embodiments, the retention layer includes PEO having MW of no less than 1000 kDa (e.g. 1000 kDa, 2000 kDa, 4000 kDa, 5000 kDa, 6000 kDa, 7000 kDa, 8000 kDa) and cellulose acetate. Exemplary ratio between the PEO and cellulose acetate includes about 10:1, about 8:1, about 6:1, about 4:1, about 3:1, about 2:1, about 1:1, and about 1:2. The amount of the PEO and cellulose acetate in the retention layer independently ranges from about 5% to about 40%, from about 10% to about 30%, from about 15% to about 30%, from about 20% to about 30%, or from about 15% to about 20%.

In some embodiments, the retention layer further includes a low viscosity hypromellose in an amount ranging from about 20% to about 50%, or about 30% to about 40%, wherein the low viscosity hypromellose has a viscosity of less than 150, less than 100, or less than 50 mPa·S.

The dosage form of this patent document may include polymers including, but not limited to, hydrophilic polymers having swelling and/or mucoadhesive properties to further promote gastroretention.

Hydrophilic polymers having swelling and or mucoadhesive properties suitable for incorporation in the compositions of present invention include, but are not limited to, polyalkylene oxides; cellulosic polymers; acrylic acid and methacrylic acid polymers, and esters thereof, maleic anhydride polymers; polymaleic acid; poly(acrylamides); poly(olefinic alcohol)s; poly(N-vinyl lactams); polyols; polyoxyethylated saccharides; polyoxazolines; polyvinylamines; polyvinylacetates; polyimines; starch and starch-based polymers; polyurethane hydrogels; chitosan; polysaccharide gums; zein; shellac-based polymers; polyethylene oxide, hydroxypropyl cellulose, hydroxypropyl methyl cellulose, hydroxyethyl cellulose, sodium carboxy methylcellulose, calcium carboxymethyl cellulose, methyl cellulose, polyacrylic acid, maltodextrin, pre-gelatinized starch and polyvinyl alcohol, chitosan, copolymers and mixtures thereof. The weight percent of the hydrophilic polymer in the dosage form of this patent document is about 5 to about 90 weight percent, preferably about 10 to about 70 weight percent, and most preferably about 15 to about 50 weight percent.

In some embodiments, the retention layer contains one or more swelling agent selected from hypromellose, hydroxypropyl cellulose, polyethylene oxide, carboxymethylcellulose, Croscarmellose Sodium, sodium starch glycolate, cross-linked povidone, and chitosan.

The dosage form described herein can take various forms. For example, in some embodiments, the gastroretentive dosage form is a bilayer or a trilayer tablet, wherein the retention layer and the active layer are compressed or otherwise joined to form a tablet structure.

The dosage form described herein may also include other pharmaceutically acceptable excipients. As is well known to those skilled in the art, pharmaceutical excipients are routinely incorporated into solid dosage forms. This is done to ease the manufacturing process as well as to improve the performance of the dosage form. The dosage form may include one or more diluents in an amount within the range of from about 0% to about 90% by weight such as, but not limited to, lactose, sugar, corn starch, modified corn starch, mannitol, sorbitol, inorganic salts such as calcium carbonate, dicalcium phosphate and/or cellulose derivatives such as wood cellulose and microcrystalline cellulose. A glidant may be used to improve powder flow properties prior to and during tableting and to reduce caking. Suitable glidants include, but are not limited to, colloidal silicon dioxide, talc, magnesium trisilicate, powdered cellulose, talc, tribasic calcium phosphate and the like. The dosage form may include lubricants such as, but not limited to, magnesium stearate, stearic acid, palmitic acid, calcium stearate, talc, polyethylene glycol, colloidal silicon dioxide, sodium stearyl fumarate, carnauba wax and the like or any combinations thereof in an amount from about 0.2% to about 8% by weight of the composition. The dosage form may further include suitable binders selected from but not limited to starch, polyethylene glycol, polyvinylpyrrolidone, hydroxypropyl methyl cellulose, hydroxypropylcellulose, natural and synthetic gums, corn starch, potato starch, or other starches, gelatin, natural and synthetic gums such as acacia, sodium alginate, alginic acid, other alginates, powdered tragacanth, guar gum, cellulose and its derivatives (e.g. ethyl cellulose, cellulose acetate, carboxymethyl cellulose calcium, sodium carboxymethyl cellulose), polyvinyl pyrrolidone, methyl cellulose, pre-gelatinized starch, microcrystalline cellulose, and mixtures thereof. The dosage form may also include stabilizers such as, but not limited to, benzoic acid, sodium benzoate, citric acid, and the like. Examples of surfactants include, but are not limited to, sodium docusate, glyceryl monooleate, polyethylene alkyl ether, polyoxyethylene sorbitan fatty acid ester, sodium lauryl sulfate, sorbic acid, sorbitan fatty acid ester, poloxamer (triblock copolymers composed of a central hydrophobic chain of polyoxypropylene (poly(propylene oxide)) flanked by two hydrophilic chains of polyoxyethylene (poly(ethylene oxide)), and mixtures thereof. Non-limiting examples of fillers suitable for use in the dosage forms disclosed herein include talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the dosage form to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art.

Disintegrants that may be used herein include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

The dosage form swells after being administered to the subject such that an average dimension of the swollen dosage form is greater than 10 mm within 1, 2, 3, 4, 5, 6, 8, 10, 15, or 20 hour and the swollen dosage form maintains integrity in said solution for at least 2, at least 3, at least 4, at least 5, at least 6, at least 8, at least 10, or at least 15 hours. In some embodiments, the dosage form remains afloat in the stomach for at least 1, at least 2, at least 3, at least 4, at least 5, at least 6, at least 8, at least 10, or at least 15 hours when the average dimension of the swollen dosage form may or may not be greater than 10 mm. After the dosage form no longer floats in the gastric fluid due to gradual disintegration, the dosage form maintains an average dimension bigger than the pyloric diameter for at least 1, at least 2, at least 3, at least 4, at least 5, at least 6 or at least 8 hours.

In some embodiments, the dosage form floats in the gastric fluid for at least 2, at least 3, at least 5, at least 6, or at least 8 hours, and after it no longer floats in the stomach, it maintains an average dimension bigger than the pyloric diameter for at least 1, 2, 3, 4, 5, or 6 hours.

One or more additional layers are optionally included into the dosage form. For instance, the API layer containing the active ingredient can be sandwiched between two retention layers. The two retention layers may have the same or different role contributing to the overall retention of the dosage form in the stomach in unfed or fed mode. In some embodiments, one layer serves to keep the dosage form afloat in the stomach for a certain period of time while a separate layer maintains the size of the dosage form bigger than the pyloric diameter of the stomach in unfed or fed mode. In some embodiments, the retention layer does not include the API or therapeutic agent. In some embodiments, the retention layer includes the API or therapeutic agent.

Alternatively, two layers each containing the active ingredient can be attached to a central retention layer. For instance, one of the two layers includes the active ingredient in the extended release form while the other contains an immediate release active ingredient. The amount of the active ingredient in the immediate release layer ranges from about 1 to about 50 mg, from about 1 to about 30 mg, from about 1 to about 20 mg, from about 1 to about 10 mg, from about 10 to about 50 mg, from about 10 to about 20 mg, from about 5 to about 10 mg, or from about 1 to about 5 mg.

When multiple layers of the dosage form contain the therapeutic agent or serve as the retention layers, the amount or ratio of excipients in each layer can be the same as in a two layer system (first layer for API and second for retention). However, the amount or ratio can also be adjusted according to the number of layers. For example, if the dosage form contains two API layers, the amount of the therapeutic agent in each API layer can be half of that in a dosage form having only a single API layer.

The dosage forms disclosed herein can be prepared by suitable methods of pharmaceutical manufacturing. In general, the dosage forms are prepared by wet granulation via high shear granulation process or fluid bed granulation process, or dry granulation via roller compaction, followed by tablet compression on a rotary tablet press, and film coating in a pan coater.

In some embodiments, the one or more excipients in the retention layer are selected that the length and width of the retention layer independently expands by about 5%, by about 10%, by about 15%, or by about 20% within about 30 minutes. In some embodiments, the length and width of the retention layer independently expands by about 30%, by about 35%, by about 40%, by about 45%, by about 50%, or by about 60% within about 2 hours, within about 6 hours, within about 8 hours, within about 16 hours or within about 24 hours. In some embodiments, the length exceeds 18 mm and/or the width of the dosage form exceeds 10 mm in the medium within 30 minutes, within 1 hour, within 2 hours, within 3 hours, within 4 hours, within 5 hours, within 6 hours, within 8 hours, within 16 hours, within 20 hours, or within 24 hours.

In some embodiments, the dosage form further comprises a coating comprising a polymer. Nonlimiting examples of the polymer include hypromellose, polyvinyl alcohol, polyvinyl alcohol-polyethylene glycol graft-copolymer, amino methacrylate copolymer, and any combination thereof. In exemplary embodiments, polymers are dissolved in water along with glidant and plasticizer. The polymer dispersion can be sprayed and coated on the tablets for example in a perforated pan coater.

In some embodiments, the API layer further includes a surfactant which preferably has a HLB value of higher than 8, higher than 9, higher then 10, higher than 12, higher than 15, higher than 18, or higher than 20. Nonlimiting examples of the surfactant include sodium lauryl sulfate and poloxamer.

Another aspect of this document provides a method of treating a disease in a subject, comprising administering to the subject the dosage form described herein. Diseases or disorders ameliorated by the inhibition of TNF-α production in mammals include, but are not limited to: HIV: hepatitis: adult respiratory distress syndrome; bone resorption diseases; chronic obstructive pulmonary diseases; chronic pulmonary inflammatory diseases; asthma; dermatitis: cystic fibrosis; septic shock: sepsis; endotoxic shock: hemodynamic shock; sepsis syndrome; post ischemic repertusion injury; meningitis: psoriasis: psoriatic arthritis; ankylosing spondylitis; Behcet's Disease; fibrotic disease; cachexia: graft rejection; auto immune disease; rheumatoid spondylitis; arthritic conditions, such as psoriatic arthritis, rheumatoid arthritis and osteoarthritis: osteoporosis; Crohn's disease; ulcerative colitis; inflammatory bowel disease; multiple sclerosis: systemic lupus erythematosus; cutaneous lupus erythematosus: pulmonary sarcoidosis; erythema nodosum leprosum (ENL) in leprosy; radiation damage; asthma; and hyperoxic alveolar injury. Such disorders further include, but are not limited to, cancers, including, but not limited to cancer of the head, thyroid, neck, eye, skin, mouth, throat, esophagus, chest, bone, blood, bone marrow, lung, colon, sigmoid, rectum, stomach, prostate, breast, ovaries, kidney, liver, pancreas, brain, intestine, heart, adrenal, subcutaneous tissue, lymph nodes, heart, and combinations thereof. Specific cancers that can be treated by this method are multiple myeloma, malignant melanoma, malignant glioma, leukemia and solid tumors. In some embodiments, the diseases include for example psoriasis, ankylosing spondylitis, Behcet's disease, rheumatoid arthritis, atopic dermatitis, Crohn's disease, ulcerative colitis.

In some embodiments, provided herein are methods of treating or preventing cancer, including but not limited to, solid tumor, blood-borne tumor, leukemias, and in particular, multiple myeloma in a subject which comprises administering to a subject in need of such treatment or prevention a dosage form disclosed herein; in particular wherein the subject is a mammal.

In some embodiments, provided herein are methods of inhibiting PDE4 which comprises contacting PDE4 in a cell (e.g. a mammalian cell) with a dosage form disclosed herein. In some embodiments, the contacting take place in a human subject.

In some embodiments, provided herein are methods of treating or preventing diseases or disorders ameliorated by the inhibition of PDE4 in a subject which comprises administering to a subject in need of a dosage form disclosed herein. Disorders ameliorated by the inhibition of PDE4 include, but are not limited to, asthma, inflammation (e.g., inflammation due to reperfusion), chronic or acute obstructive pulmonary diseases, chronic or acute pulmonary inflammatory diseases, cutaneous lupus erythematosis, inflammatory bowel disease, Crohn's Disease, Behcet's Disease, or colitis.

In some embodiments, provided herein are methods of controlling cAMP levels in a cell which comprises contacting a cell with a dosage form provided herein, or a pharmaceutically acceptable prodrug, metabolite, polymorph, solvate, hydrate, or clathrate thereof. As used herein the term "controlling cAMP levels" includes preventing or reducing the rate of the breakdown of Adenosine 3',5'-cyclic monophosphate (cAMP) in a cell or increasing the amount of Adenosine 3',5'-cyclic monophosphate present in a cell, preferably a mammalian cell, more preferably a human cell. In some embodiments, the contacting take place in a human subject.

In some embodiments, provided herein are methods of treating or preventing depression, asthma, inflammation, contact dermatitis, atopic dermatitis, psoriasis, psoriatic arthritis, rheumatoid arthritis, osteoarthritis, cutaneous lupus erythematosis, ankylosing spondylitis, inflammatory skin disease, inflammation due to reperfusion, chronic or acute obstructive pulmonary diseases, chronic or pulmonary inflammatory diseases, autoimmune diseases, inflammatory bowel disease, Crohn's Disease, Behcet's Disease or colitis in a patient which comprises administering to a subject in need of a dosage form disclosed herein.

In some embodiments, provided herein are methods of treating or preventing myelodysplastic syndrome (MDS) which comprises administering to a subject in need of a dosage form disclosed herein. MDS refers to a diverse group of hematopoietic stem cell disorders. MDS is characterized by a cellular marrow with impaired morphology and maturation (dysmyelopoiesis), peripheral blood cytopenias, and a variable risk of progression to acute leukemia, resulting from ineffective blood cell production.

In some embodiments, provided herein are methods of treating or preventing myeloproliferative disease (MPD) which comprises administering to a subject in need of a dosage form disclosed herein. Myeloproliferative disease (MPD) refers to a group of disorders characterized by clonal abnormalities of the hematopoietic stem cell.

In some embodiments, provided herein are methods of treating, preventing or managing pain, including, but not limited to, complex regional pain syndrome, which comprises administering to a subject in need of a dosage form disclosed herein. In a specific embodiment, the administration is before, during or after surgery or physical therapy directed at reducing or avoiding a symptom of complex regional pain syndrome in the subject.

In some embodiments of any method disclosed herein, the dosage form is administered with food, which is e.g., a high fat food or a high fat and/or high calorie meal. The term "high fat meal" refers generally to a meal of at least about 700 kcal and at least about 45% fat (relative percentage of kcal which are fat), or alternatively at least about 900 kcal and at least about 50% fat. The term "high fat food" refers generally to a food comprising at least 20 g of fat, or at least 25, 30, 35, 40, 45, or 50 g of fat, and/or at least about 45% or 50% fat. One FDA Guidance defines a "high-fat meal" as approximately 50% of total caloric content of the meal, whereas a "high-calorie meal" is approximately 800 to 1000 calories. The FDA recommends a high-fat and high-calorie meal as a test meal for food-effect bioavailability and fed bioequivalence studies. This test meal should derive approximately 150, 250, and 500-600 calories from protein, carbohydrate and fat, respectively. An example test meal consists of two eggs fried in butter, two strips of bacon, four ounces of hash brown potatoes and eight ounces of whole milk. Substitution is possible if a similar amount of calories from protein, carbohydrate, and fat has comparable meal volume and viscosity (Guidance for Industry, Food-Effect Bioavailability and Fed Bioequivalence Studies, U.S. Department of Health and Human Services, Food and Drug Administration, Center for Drug Evaluation and Research (CDER), December 2002).

The dosage form and the food may be ingested at approximately the same time, or the dosage from may be ingested before or after the food. In some embodiments, the period of time between consuming food, e.g., a high-fat food or a high-fat and/or high-calorie meal and taking the dosage form swallowed may be no more than 2 minutes, no more than 5 minutes, no more than 10 minutes, no more than 15 minutes, no more than 15 minutes, no more than 20 minutes, no more than 25 minutes, no more than 30 minutes, no more than 40 minutes, or no more than 60 minutes. In some embodiments, the dosage form may be administered 60 minutes, 30 minutes, 25 minutes, 20 minutes, 15 minutes, 10 minutes, or 5 minutes after ingestion of a meal.

In some embodiments of any methods disclosed here, there is a step of informing the subject that administration of the dosage form with food has an effect on pharmacokinetics. In some embodiments, the methods comprise the step of informing the patient that absorption of the dosage from is increased when it is ingested with food compared to when ingested without food. In some embodiments, the patient is informed that ingestion shortly following a meal, for example, a high-fat, high-calorie meal, results in an increase in any one, two, or all of the following parameters: mean plasma concentration, Cmax, AUC. In some embodiments, the administration of the dosage from with a high-fat meal increases Cmax and AUC compared to administration of the dosage from without food (in a fasting condition). In some embodiments, the relative increase is at least 20% or at least 30% or more.

In some embodiments of any method disclosed herein, the dosage form is administered once daily. The amount of API or equivalent amount of the pharmaceutically acceptable amorphous, polymorph, solvate or hydrate thereof is as described above.

In some embodiments of any method disclosed herein, the method further includes administering to the subject an additional agent selected from the group consisting of anti-inflammatories (e.g. NSAIDs), immunosuppressants, topical corticosteroids, calcineurin inhibitors, Cox-2 inhibitors, TNF-alpha inhibitors, antirheumatics, antipsoriatics, interleukin inhibitors, narcotic analgesic combinations, salicylates, glucocorticoids and topical rubefacients. The additional agent may be incorporated in the dosage form. Alternatively, the additional agent may be in a separate dosage form of its own. In some embodiments, the additional agent is administered together with the dosage form disclosed herein. In some embodiments, the additional agent is administered before or after the administration of the dosage form disclosed herein.

In some embodiments, the second active agent is selected from the group consisting of an anti-inflammatory agent, an immunosuppressant, mycophenolate mofetil, a biologic agent, or a Cox-2 inhibitor.

In some embodiments, the second active agent is sulfasalazine. In some embodiments, the second active agent is leflunomide. In some embodiments, the second active agent is an oral corticosteroid. In some embodiments, the second active agent is etanercept.

In some embodiments, the second active agents may include, but are not limited to, anti-inflammatories such as NSAIDs including, but not limited to, diclofenac (e.g., ARTHROTEC®), diflunisal (e.g., DOLOBID®), etodolac (e.g., LODINE®), fenoprofen (e.g., NALFON®), ibuprofen (e.g., ADVIL, CHILDREN'S ADVIL/MOTRIN, MEDIPREN, MOTRIN, NUPRIN or PEDIACARE FEVER®), indomethacin (e.g., ARTHREXIN®), ketoprofen (e.g., ORUVAIL®), ketorolac (e.g., TORADOL®), fosfomycin tromethamine (e.g., MONURAL®), meclofenamate (e.g., Meclomen®), nabumetone (e.g., RELAFEN®), naproxen (e.g., ANAPROX®, ANAPROX® DS, EC-NAPROSYN®, NAPRELAN® or NAPROSYN®), oxaprozin (e.g., DAYPRO®), piroxicam (e.g., FELDENE®), sulindac (e.g., CLINORIL®), and tolmetin (e.g., TOLECTIN® DS or TOLECTIN®).

In other embodiments, the second active agents may include, but are not limited to, disease-modifying antirheumatic drugs (DMARDs) or immunosuppressants such as, but not limited to, methotrexate (Rheumatrex®), sulfasalazine (Azulfidine®), leflunomide (Arava®), and cyclosporine (Sandimmune® or Neoral®).

In other embodiments, the second active agent is an oral corticosteroid, such as, but not limited to, budesonide (Entocort®), dexamethasone, fludrocortisone (Florinef®, Florinef® acetate), hydrocortisone, methylprednisone, prednisolone, and prednisone.

In other embodiments, the second active agents may include, but are not limited to, mycophenolate mofetil (CellCept®), an immunosuppressive agent widely used in organ transplantation and gaining favor in treating autoimmune and inflammatory skin disorders.

In further embodiments, the second active agents may include, but are not limited to, biologic agents such as etanercept (Enbrel®), infliximab (Remicade®) and adalimumab (Humira®).

In further embodiments, the second active agents may include, but are not limited to, Cox-2 inhibitors such as celecoxib (Celebrex®), valdecoxib (Bextra®) and meloxicam (Mobic®).

In some embodiments, the one or more selective active agents is selected from the group consisting of acitretin, adalimumab, alclometasone, alefacept, aloe vera, amcinonide, ammonium lactate/urea, ammonium lactate/halobetasol, anthralin, benzocaine/pyrilamine/zinc oxide, betamethasone, betamethasone/calcipotriene, calcipotriene, clobetasol, clocortolone, coal tar, coal tar/salicylic acid, corticotropin, cyclosporine, desonide, desoximetasone, diflorasone, fluocinonide, flurandrenolide, halcinonide, halobetasol, hydrocortisone, hydrocortisone/pramoxine, hydroxyurea, infliximab, methotrexate, methoxsalen, mometasone, pramoxine, prednisone, prednisolone, prednicarbate, resorcinol, tazarotene, triamcinolone and ustekinumab.

In some embodiments, the one or more selective active agents is selected from the group consisting of abatacept, acetaminophen, acetaminophen/hydrocodone, acetaminophen/tramadol, adalimumab, alemtuzumab, aluminum hydroxide/aspirin/calcium carbonate/magnesium hydroxide, anakinra, aspirin, auranofin, aurothioglucose, atorvastatin, azathioprine, celecoxib, certolizumab, chondroitin, cortisone, corticotropin, cyclophosphamide, cyclosporine, daclizumab, dexamethasone, diclofenac, diclofenac/misoprostol, diflunisal, doxycycline, esomeprazole, esomeprazole/naproxen, etanercept, etodolac, famotidine, famotidine/ibuprofen, fenoprofen, flurbiprofen, glucosamine, gold sodium thiomalate, golimumab, hydroxychloroquine, ibuprofen, indomethacin, infliximab, interferon, interferon gamma-1b, ketoprofen, lansoprazole, lansoprazole/naproxen, leflunomide, levamisole, meclofenamate, meloxicam, methotrexate, methylprednisone, methylprednisolone, methyl salicylate, minocycline, mycophenolate mofetil, nabumetone, naproxen, oxaprozin, penicillamine, phenytoin, piroxicam, prednisone, primrose oil, rituximab, rofecoxib, salsalate, sulindac, sulfasalazine, tetracycline, tocilizumab, tofacitinib, tolmetin, tramadol, triamcinolone, trolamine salicylate, valdecoxib and pharmaceutically acceptable prodrugs and salts thereof.

In some embodiments, the one or more selective active agents is selected from the group consisting of abatacept, acetaminophen, acetaminophen/hydrocodone, acetaminophen/tramadol, acitretin, adalimumab, alclometasone, alefacept, alemtuzumab, aloe vera, aluminum hydroxide/aspirin/calcium carbonate/magnesium hydroxide, amcinonide, ammonium lactate/urea, ammonium lactate/halobetasol, anakinra, anthralin, aspirin, auranofin, aurothioglucose, atorvastatin, azathioprine, benzocaine/pyrilamine/zinc oxide, betamethasone, betamethasone/calcipotriene, calcipotriene, celecoxib, certolizumab, chondroitin, clobetasol, clocortolone, coal tar, coal tar/salicylic acid, corticotropin, cortisone, cyclophosphamide, cyclosporine, daclizumab, desonide, desoximetasone, dexamethasone, diclofenac, diclofenac/misoprostol, diflorasone, diflunisal, doxycycline, esomeprazole, esomeprazole/naproxen, etanercept, etodolac, famotidine, famotidine/ibuprofen, fenoprofen, fluocinonide, flurandrenolide, flurbiprofen, fostamatinib, glucosamine, gold sodium thiomalate, golimumab, halcinonide, halobetasol, hydrocortisone, hydrocortisone/pramoxine, hydroxyurea, hydroxychloroquine, ibuprofen, indomethacin, infliximab, interferon, interferon gamma-1b, ibrutinib, ketoprofen, lansoprazole, lansoprazole/naproxen, leflunomide, lenalidomide, levamisole, meclofenamate, meloxicam, methotrexate, methoxsalen, methylprednisone, methylprednisolone, methyl salicylate, minocycline, mometasone, mycophenolate mofetil, nabumetone, naproxen, oxaprozin, penicillamine, phenytoin, piroxicam, pomalidomide, pramoxine, prednisone, prednisolone, prednicarbate, primrose oil, resorcinol, rituximab, rofecoxib, salsalate, sulindac, sulfasalazine, tazarotene, tetracycline, tocilizumab, tofacitinib, tolmetin, tramadol, triamcinolone, trolamine salicylate, ustekinumab, valdecoxib, 3-(5-amino-2-methyl-4-oxo-4H-quinazolin-3-yl)-piperidine-2,6-dione, (S)-3-(4-((4-(morpholinomethyl)benzyl)oxy)-1-oxoisoindolin-2-yl)piperidine-2,6-dione and pharmaceutically acceptable prodrugs and salts thereof.

In some embodiments, the one or more selective active agents is selected from the group consisting of a PDE7 inhibitor, a Btk inhibitor, a cereblon targeting agent, a Tyk2 inhibitor, a Syk inhibitor, a JAK inhibitor, a JNK inhibitor, a MK2 inhibitor, an ERP5 inhibitor, a PD-1 inhibitor, a TIMP-3 inhibitor, an IL23p19 inhibitor, an IL-17 blocker, an IKK-2 inhibitor, a LH2B inhibitor, a PKC-theta inhibitor, an IRAK4 inhibitor, a ROCK inhibitor, and a ROR-gamma-T inhibitor.

The amount of second active agent administered can be determined based on the specific agent used, the subject being treated, the severity and stage of disease and the amount(s) of apremilast and any optional additional second active agents concurrently administered to the patient. Those of ordinary skill in the art can determine the specific amounts according to conventional procedures known in the art. In the beginning, one can start from the amount of the second active agent that is conventionally used in the therapies and adjust the amount according to the factors described above. See, e.g., Physician's Desk Reference (59th Ed., 2005).

In certain embodiments, the second active agent is administered orally, topically, transdermally, intravenously or subcutaneously. In certain embodiments, the second active agent is administered once to four times daily. In certain embodiments, the second active agent is administered once to four times monthly. In certain embodiments, the second active agent is administered once every week. In certain embodiments, the second active agent is administered once every other week. In certain embodiments, the second active agent is administered once every month. In certain embodiments, the second active agent is administered once every two months. In certain embodiments, the second active agent is administered once every three months. In certain embodiments, the second active agent is administered in an amount of from about 1 to about 1,000 mg, from about 5 to about 500 mg, from about 10 to about 350 mg or from about 50 to about 200 mg. The specific amount of the second active agent will depend on the specific agent used, the age of the subject being treated, the severity and stage of disease and the amount(s) of apremilast and any optional additional second active agents concurrently administered to the patient.

Another aspect of the patent document discloses a method of providing in a subject an area under curve (AUC in a 0 to 24 hour period or 0 to ∞ infinity) of a first therapeutic agent ranging from about 70% to about 125% (e.g. 70%, 75%, 80%, 85%, 90%, 95%, 100%, 105%, 110%, 115%, 120%, or 125%) of the AUC of the first therapeutic agent administered BID as an immediate release formulation. The first therapeutic agent administered BID as an immediate release formulation is used as a reference. The method includes administering to the subject once a day the dosage form disclosed herein, wherein the amount of the first therapeutic agent in the dosage form ranges from about 60% to about 150% (e.g. 60%, 65%, 70%, 75%, 80%, 85%, 90%, 95%, 100%, 105%, 110%, 115%, 120%, 125%, 130%, 140%, or 150%) of the daily total amount of the first therapeutic agent in the immediate release formulation.

In some embodiments of the method, the amount of the first therapeutic agent in the dosage form ranges from about 80% to about 120% (e.g. 80%, 85%, 90%, 95%, 100%, 105%, 110%, 115%, or 120%) of the daily total amount of the first therapeutic agent in the immediate release formulation. In some embodiments, the dosage from provides Cn of the first therapeutic agent ranging from about 70% to about 150% (e.g. 70%, 65%, 70%, 75%, 80%, 85%, 90%, 95%, 100%, 105%, 110%, 115%, 120%, 125%, 130%, 140%, or 150%) of the $C_{max}$ of the first therapeutic agent administered BID as an immediate release formulation. In some embodiments, the dosage from provides $C_{max}$ of the first therapeutic agent ranging from about 80% to about 120% of the $C_{max}$ of the first therapeutic agent administered BID as an immediate release formulation.

In some embodiments, the amount of the first therapeutic agent in the dosage form ranges from about 80% to about 120% (e.g. 80%, 85%, 90%, 95%, 100%, 105%, 110%, 115%, or 120%) of the daily total amount of the first therapeutic agent in the immediate release formulation, wherein the first therapeutic agent is apremilast. In some embodiments, the amount of the first therapeutic agent in the dosage form and the daily amount of the first therapeutic agent in the immediate release formulation are each 60 mg, wherein the first therapeutic agent is apremilast.

In some embodiments, the amount of the first therapeutic agent in the dosage form ranges from about 8 mg to about 15 mg (e.g. 8, 10, 12, 14 or 15 mg) and the daily total amount of the first therapeutic agent in the immediate release formulation is about 10 mg, wherein the first therapeutic agent is tofacitinib. In some embodiments, the amount of the first therapeutic agent in the dosage form ranges from about 15 mg to about 25 mg (e.g. 15, 18, 20, 22 or 25 mg) and the daily total amount of the first therapeutic agent in the immediate release formulation is about 20 mg, wherein the first therapeutic agent is tofacitinib.

In some embodiments, the dosage form is administered with food. In some embodiments, the subject has been diagnosed to have a disease described above. In some embodiments, the subject has been diagnosed to have a disease selected from psoriasis, ankylosing spondylitis, Behcet's disease, rheumatoid arthritis, atopic dermatitis, Crohn's disease, and ulcerative colitis. In some embodiments, the subject is human.

In any embodiments disclosed herein, a reference as an immediate release form may be administered with food, without food, or under fasting condition for the patient. In some embodiments, the reference is an immediate release from of apremilast or tofacitinib.

In any of the methods disclosed herein, administration of the dosage form and a second active agent to a patient can occur simultaneously or sequentially by the same or different routes of administration. The suitability of a particular route of administration employed for a particular second active agent will depend on the second active agent itself (e.g., whether it can be administered orally or topically without decomposing) and the subject being treated. Particular routes of administration for the second active agents or ingredients are known to those of ordinary skill in the art. See, e.g., The Merck Manual, 448 (17th ed., 1999).

Another aspect of the patent document provides a method of preparing the dosage form disclosed herein. The method generally includes preparation of one or more API layers and one or more retention layers, followed by the compression of the two types of layers and then optionally a coating step. The API, ingredients, excipients, and their respective amounts and ratios for the production are as described above.

In some embodiments, the preparation of the retention layer includes passing the excipients through a mill and mixing the excipients. In some embodiments, the preparation of the API layer includes passing the API and intra-granular excipients though a mill and forming an intra-granular portion, which is then mixed with extra-granular excipients to form the API layer. The preparation of the dosage form may incorporate any step of the exemplified manufacturing in the example section below.

The following non-limiting examples illustrate the invention:

Example 1. Apremilast Triple Layer Gastroretentive ER Tablets

Apremilast (crystalline Form B) Trilayer tablets are examined in this example. The retention layer is sandwiched between two layers containing Apremilast crystalline Form B. Alternatively, the API layer can be flanked by two retention layers.

The Trilayer tablets were made manually on a single punch tablet press (Globepharma Manual Tablet Compaction Machine, MTCM-I). The five formulations were developed with same retention layer formulation but different API layer formulations, which are composited by different drug release retarding agents, ex Hypromellose viscosity 100 mPa·S (measured at 2% concentration in water at 20° C.), and Hypromellose viscosity 3 mPa·S. Drug release can be increased by reducing Hypromellose viscosity 100 mPa·S amount and using Low-substituted hydroxypropylcellulose to replace lactose monohydrate. The drug release could be slightly reduced by using Amino Methacrylate Copolymer and Povidone (polyvinylpyrrolidone) to replace silicified microcrystalline cellulose as comparing Lot 004 with 005. The wetting agents investigated were Sodium Lauryl Sulfate and Poloxamer (a nonionic triblock copolymers composed of a central hydrophobic chain of polyoxypropylene flanked by two hydrophilic chains of polyoxyethylene). The drug release was slightly faster by using Poloxamer than SLS as comparing Lot 003 with Lot 004.

TABLE 1

Apremilast Layer Formula for Triple layer Tablet

| Ingredients | mg/Tablet | | | | |
|---|---|---|---|---|---|
| Lot | 001 | 002 | 003 | 004 | 005 |
| Apremilast Crystalline Form B | 60 | 60 | 60 | 60 | 60 |
| Sodium Lauryl Sulfate | 10 | 0 | 0 | 10 | 10 |
| Poloxamer | 0 | 0 | 10 | 0 | 0 |
| Amino Methacrylate Copolymer | 0 | 0 | 0 | 0 | 30 |
| Povidone | 0 | 0 | 0 | 0 | 20 |
| Hypromellose viscosity 3 mPa·S | 0 | 0 | 86 | 86 | 86 |
| Hypromellose viscosity 100 mPa·S | 70 | 70 | 50 | 50 | 50 |
| Low-substituted hydroxypropylcellulose | 0 | 0 | 100 | 100 | 100 |
| Lactose monohydrate | 100 | 100 | 0 | 0 | 0 |
| Silicified microcrystalline cellulose | 156 | 166 | 90 | 90 | 40 |
| Magnesium Stearate | 4 | 4 | 4 | 4 | 4 |
| Total API layer | 400 | 400 | 400 | 400 | 400 |

TABLE 2

Retention Layer Formula

| Ingredients | Lot 006, % |
|---|---|
| Cellulose Acetate | 10.0 |
| Poly(ethylene oxide) 7,000,000 molecular weight | 48.8 |

TABLE 2-continued

Retention Layer Formula

| Ingredients | Lot 006, % |
|---|---|
| Hypromellose viscosity 3 mPa·S | 2.0 |
| Hypromellose viscosity 100,000 mPa·S | 32.8 |
| Silicified microcrystalline cellulose | 5.3 |
| Magnesium Stearate | 1.1 |
| Total, Core | 100 |

TABLE 3

Apremilast Trilayer Tablet Composition

| Ingredients | mg Tablet | | | | |
|---|---|---|---|---|---|
| Lot | 001 | 002 | 003 | 004 | 005 |
| Layer 1 - API layer | 200 | 200 | 200 | 200 | 200 |
| Layer 2 - Retention Layer | 300 | 300 | 300 | 300 | 300 |
| Layer 3 - API layer | 200 | 200 | 200 | 200 | 200 |
| Total Trilayer Tablet | 700 | 700 | 700 | 700 | 700 |

TABLE 4

Dissolution in 900 mL pH 4.5, 50 mM Acetate buffer with 2% Tween 80 by Paddles over disc, 75 rpm

| Time (h) | 001 | 002 | 003 | 004 | 005 |
|---|---|---|---|---|---|
| 1 | 21 | 26 | 21 | 17 | 17 |
| 2 | 30 | 36 | 39 | 32 | 34 |
| 4 | 45 | 51 | 65 | 55 | 60 |
| 6 | 56 | 63 | 80 | 73 | 74 |
| 8 | 67 | 73 | 87 | 87 | 82 |
| 12 | 78 | 85 | 94 | 95 | 87 |
| 16 | 81 | 91 | 97 | 97 | 91 |
| 20 | 88 | 94 | 98 | 99 | 93 |
| 24 | 93 | 96 | 99 | 100 | 93 |

Example 2. Apremilast (Form B) Bilayer Gastroretentive ER Tablets

The innovated bilayer tablet is combined with an API layer and a retention layer. Apremilast (Form B or Amorphous Form) were used as API for the investigations. During the dissolution, the drug release rate and extent are controlled by the API layer system. The retention layer is quickly hydrated, swelling, expanding to have a bulk density less than gastric fluids, hence generating buoyancy, which enable the tablet floating on the surface of the dissolution medium. The floating lag time of the current gastroretentive tablets in vitro is within 30 minutes and floating time is at least 16 hours. In the in vivo condition, gastric retentive or floating drug delivery systems have a bulk density less than gastric fluids and so remain buoyant in the stomach without affected by the gastric emptying rate for a prolonged period of time, while the system is floating or retention on the gastric contents.

2.1 Single Punch Tablet Press

Bilayer tablets composed of the retention layer, and API layer were compressed manually on a single punch tablet press (Globepharma Manual Tablet Compaction Machine, MTCM-I). Four formulations were designed to provide different drug release rate profiles from 12 hours to 24 hours. The drug release rate is adjusted by changing the ratio of Hypromellose viscosity 100 mPa·S to Hypromellose viscosity 3 mPa·S. The two water soluble polymers are Hypromellose, but they have different viscosities: 3 mPa·S and 100 mPa·S, respectively. The drug release rate is decreased with increasing Hypromellose viscosity 100 mPa·S ratio in the formulations (see Table 5, Table 6).

TABLE 5

Formulations of the Bilayer Tablets

| | Tablet Design | Trial 007A mg/Tablet | Trial 007B mg/Tablet | Trial 007C mg/Tablet | Trial 007D mg/Tablet |
|---|---|---|---|---|---|
| API layer | Apremilast Form B | 60 | 60 | 60 | 60 |
| | Poloxamer | 10 | 10 | 10 | 10 |
| | Hypromellose viscosity 3 mPa·S | 86 | 66 | 46 | 86 |
| | Hypromellose viscosity 100 mPa·S | 50 | 70 | 90 | 30 |
| | Low-substituted hydroxypropylcellulose | 100 | 100 | 100 | 100 |
| | Silicified microcrystalline cellulose | 90 | 90 | 90 | 110 |
| | Magnesium Stearate | 4 | 4 | 4 | 4 |
| | API layer total | 400 | 400 | 400 | 400 |
| Retention Layer | Colorants | 3 | 3 | 3 | 3 |
| | Cellulose Acetate | 45 | 45 | 45 | 45 |
| | Citric Acid | 60 | 60 | 60 | 60 |
| | Sodium bicarbonate | 30 | 30 | 30 | 30 |
| | Poly(ethylene oxide) 7,000,000 molecular weight | 252 | 252 | 252 | 252 |

TABLE 5-continued

Formulations of the Bilayer Tablets

| Tablet Design | Trial 007A mg/Tablet | Trial 007B mg/Tablet | Trial 007C mg/Tablet | Trial 007D mg/Tablet |
|---|---|---|---|---|
| Hypromellose viscosity 3 mPa · S | 12 | 12 | 12 | 12 |
| Hypromellose viscosity 100,000 mPa · S | 162 | 162 | 162 | 162 |
| Silicified microcrystalline cellulose | 30 | 30 | 30 | 30 |
| Magnesium Stearate | 6 | 6 | 6 | 6 |
| Retention Layer | 600 | 600 | 600 | 600 |
| Total | 1000 | 1000 | 1000 | 1000 |

TABLE 6

Dissolution method: paddle over disk (900 mL pH 4.5 + 2% tween 80 at 37° C.), 75 rpm

| Time(h) | Trial 007D | Trial 007A | Trial 007B | Trial 007C |
|---|---|---|---|---|
| 1 | 19 | 11 | 5 | 5 |
| 2 | 40 | 22 | 13 | 9 |
| 4 | 67 | 39 | 26 | 16 |
| 6 | 84 | 55 | 38 | 23 |
| 8 | 90 | 68 | 49 | 31 |
| 12 | 94 | 88 | 68 | 45 |
| 16 | 95 | 96 | 83 | 60 |
| 20 | 96 | 97 | 93 | 75 |
| 24 | 96 | 97 | 96 | 88 |

2.2 Dry Granulation by Roller Compaction

Roller compaction is a unit operation in the dry granulation process. During the dry granulation process, the dry powders of the active ingredient and excipients (dry binders, polymers, disintegrates, filler, lubricants and other excipients) are mixed in a blender. The powder mixtures are roller compacted into ribbons, which are sized by a miller into granules. The granule particle size, densities, flowability and compressibility can be adjusted by changing formulation composition and process parameters of roller compactor (ex. feeder speed, roller compaction force, roller gap, roller speed, miller speed and screening size etc). Dry granulation by roller compaction has various advantages such as simplicity of manufacturing procedure, cost-advantages, easier scale up and large production output. In roller compaction process there is no liquid or drying process involved so this process is more suitable for moisture and heat sensitive drug formulation. As compared to direct compression, roller compaction process can run more efficiently with high drug loading, improve flow, and content uniformity without material segregation.

TABLE 7

Formulation: Apremilast Form B Bilayer Tablets Lot 008

| Processing | Ingredient | mg/Tab |
|---|---|---|
| API layer | Intra-granular ingredients- Roller compaction | |
| | Apremilast Form B | 60 |
| | Poloxamer | 10 |
| | Colloidal Silicon Dioxide | 4 |
| | Hypromellose (Hypromellose viscosity 100 mPa · S) | 50 |
| | Low-substituted hydroxypropylcellulose | 50 |
| | Lactose Anhydrous Impalpable | 50 |
| | Microcrystalline cellulose | 90 |
| | Hydroxypropyl Cellulose | 76 |
| | Magnesium Stearate | 2 |
| | Extra-Granular excipients | |
| | Magnesium Stearate | 4 |
| | Colloidal Silicon Dioxide | 4 |
| | API layer Weight | 400 |
| Retention Layer | Cellulose Acetate | 30 |
| | Polyethylene oxide (Poly(ethylene oxide) 7,000,000 molecular weight) | 168 |
| | Hypromellose (Hypromellose viscosity 3 mPa · S) | 8 |
| | Hypromellose (Hypromellose viscosity 100,000 mPa · S) | 108 |
| | Silicified microcrystalline cellulose | 20 |
| | Citric Acid | 40 |
| | Sodium Bicarbonate | 20 |
| | Colorant (FD&C Blue #1 Aluminum Lake 11-13%) | 2 |
| | Magnesium Stearate | 4 |
| | Retention Layer Weight | 400 |
| | Bilayer Tablet Weight | 800 |

TABLE 8

Dissolution in 900 mL pH 4.5, 50 mM Acetate buffer with 2% Tween 80 at 37° C. by Baskets, 150 rpm

| Time (h) | NS002-008 | 009 |
|---|---|---|
| 1 | 3 | 9 |
| 2 | 5 | 18 |
| 4 | 10 | 34 |
| 6 | 16 | 50 |
| 8 | 23 | 61 |
| 12 | 35 | 79 |
| 16 | 46 | 87 |
| 20 | 55 | 90 |
| 24 | 63 | 92 |

In this case, the roller compaction technology was used to improve flowability and compressibility of API layer granules. The formulation is listed in Table 7. The tablets compressed with granules of roller compaction provided significant slower drug release profile than the tablets by a direct compression process (lot 009). This is attributed to the tablets compressed with granules of roller compaction have higher density in the tablets. The drug release is adjustable by changing the composition of API layer.

2.3. Influence of Inert Fatty Materials on Drug Release and Floating Capability

Inert fatty materials are used for pharmaceutical excipients for controlled release drug delivery systems, for example hydrogenated vegetable oils, glycerides, polyoxylglycerides, ethoxylated glycerides, esters of edible fatty acids, and various alcohols are the main vegetable oil derivatives that usually contain fatty acids. In this example, glyceryl behenate (Glyceryl behenate, a mixture of glycerides of fatty acids, mainly behenic acid, with 12.0-18.0% of 1-monoglycerides) and hydrogenated vegetable oil (type I, Lubritab®) were investigated in bilayer tablets with different functional areas, for example lipid and low density excipients for drug release controlling agent, gastric retention floating agent, viscosity-increasing agent and lubricant.

The manufacturing process is carried out by five main steps listed as follows:

1) Preparation of Retention Layer Blend
   Excipients are weighed and passed through a cone mill.
   Excipients are mixed in a (bin) blender.
2) Preparation of Apremilast Layer Blend
   Apremilast and intra-granular excipients are weighed and passed through a cone mill.
   Apremilast and intra-granular excipients are mixed in a blender.
   Blend is roller compacted and milled to form granules.
   Extra-granular excipients are weighed (and passed through a cone mill).
   Extra-granular excipients and roller compacted granules are mixed in a blender.
3) Bilayer Tablet Compression
   Bilayer tablet press is set up with the capsule-shape D-toolings
   Retention layer blend and Apremilast layer blend are loaded in the hoppers.
   Bilayer tablets are compressed to the target weight and hardness.
4) Film Coating
   Bilayer tablets are coated with a film coat in a pan coater.
5) Packaging
   Apremilast ER Tablets are filled into 75 cc HDPE bottles with desiccants and induction sealed with 33 mm CRC.

Surprisingly, incorporation of Glyceryl behenate led to strong bonding between the API layer and the retention layer. Bilayer tablets demonstrated good floatability in water.

Three formulations of API layer with different levels of Glyceryl behenate were investigated and the results indicated that drug release rate could be significantly adjusted by changing the Glyceryl behenate amount from 10% w/w, 15% w/w to 20% w/w in the API layer. The d50% time point of drug release rate is about 3 hour, 8 hour and 20 hours for formulation Lot 010, Lot 011 and 012, respectively. Glyceryl behenate is a blend of different esters of behenic acid with glycerol, a mixer of hydrophobic polymers, which could form a matrix to slow down drug release.

TABLE 9

Formulation Table

| Process | Ingredient Name | 010 mg/Tab | 011 mg/Tab | 012 mg/Tab |
|---|---|---|---|---|
| API layer | Roller Compaction Ingredients | | | |
| | Apremilast Form B | 60 | 60 | 60 |
| | Poloxamer | 10 | 10 | 10 |
| | Colloidal Silicon Dioxide | 4 | 4 | 4 |
| | Lactose Anhydrous | 50 | 50 | 50 |
| | Microcrystalline cellulose | 90 | 90 | 90 |
| | Hydroxypropyl Cellulose | 76 | 76 | 76 |
| | Magnesium Stearate | 4 | 4 | 4 |
| | Total API Granules for Roller Compaction | 294 | 294 | 294 |
| | Extra-granular excipients | | | |
| | Glyceryl behenate | 33 | 74.4 | 52.5 |
| | Colloidal Silicon Dioxide | 3 | 3.7 | 3.5 |
| | API layer Weight | 330 | 372.1 | 350 |
| Retention Layer | Cellulose Acetate | 45 | 45 | 45 |
| | Polyethylene oxide (Poly(ethylene oxide) 7,000,000 molecular weight) | 252 | 252 | 252 |
| | Hypromellose (Hypromellose viscosity 3 mPa · S) | 12 | 12 | 12 |
| | Hypromellose (Hypromellose viscosity 100,000 mPa · S) | 162 | 162 | 162 |
| | Silicified microcrystalline cellulose | 30 | 30 | 30 |
| | Citric Acid | 60 | 60 | 60 |
| | Sodium Bicarbonate | 30 | 30 | 30 |
| | Colorant | 3 | 3 | 3 |
| | Magnesium Stearate | 6 | 6 | 6 |
| | Swelling Layer Weight | 600 | 600 | 600 |
| | Bilayer Tablet Weight | 930 | 972.1 | 950 |

TABLE 10

Dissolution data of Lot 010, 011, and 012: effect of Glyceryl behenate.

| Time point: hr | Lot 010 (10% Glyceryl behenate) | lot 011 (15% Glyceryl behenate) | lot 012 (20% Glyceryl behenate) |
|---|---|---|---|
| 0.5 | 9 | 7 | 4 |
| 1 | 18 | 13 | 8 |
| 2 | 34 | 22 | 12 |
| 4 | 60 | 33 | 17 |
| 6 | 83 | 40 | 21 |
| 8 | 96 | 48 | 26 |
| 12 | 102 | 65 | 35 |
| 16 | 103 | 81 | 44 |
| 20 | 104 | 91 | 50 |

While Glyceryl behenate is a partial hydrogenated vegetable oil, the hydrogenated vegetable oil is a fully hydrogenated vegetable oil products with similar chemical and physical characteristics, which may be used as alternatives to Glyceryl behenate in controlled release and gastric retentive drug delivery systems. In this case, formulation Lot 014 has the same manufacture process and the same formulation composition to Lot 013, except that Glyceryl behenate was replaced by the same amount of Lubritab, a commercial product of hydrogenated vegetable oil. The formulation of Lot 014 could provide the similar dissolution profile to formulation of Lot 013. The result indicated that hydrogenated vegetable oil and Glyceryl behenate can be used as alternatives each other in controlled release and gastric retentive drug delivery systems.

TABLE 12

Formulation composition of Lot 013 and 014

| Process | MATERIAL DESCRIPTION | LOT013 mg/Tab | Lot 014 mg/Tab |
|---|---|---|---|
| API layer Roller Compacted Granules | Apremilast Form B | 60 | 60 |
| | Poloxamer | 10 | 10 |
| | Lactose Anhydrous Impalpable | 50 | 50 |
| | Microcrystalline cellulose | 90 | 90 |
| | Hydroxypropyl Cellulose | 76 | 76 |
| | Colloidal Silicon Dioxide | 4 | 4 |
| | Magnesium Stearate | 4 | 4 |
| API layer Extra-granular | Glyceryl behenate | 37 | — |
| | Hydrogenated vegetable oil | — | 37 |
| | Hypromellose viscosity 4,000 mPa·S | 37 | 37 |
| | Colloidal Silicon Dioxide | 4 | 4 |
| | Total API layer | 372 | 372 |
| Retention Layer | Cellulose Acetate CA-398-10 NF | 89.4 | 50 |
| | Polyethylene oxide (Poly(ethylene oxide) 7,000,000 molecular weight) | 252 | 180 |
| | Hypromellose (Hypromellose viscosity 100 mPa·S DC2) | 162 | 234 |
| | Citric Acid | 36 | 36 |
| | Sodium Bicarbonate | 54 | 54 |
| | Colorant | 0.6 | 0.5 |
| | Lactose monohydrate Supertab 11SD | — | 39.5 |
| | Magnesium Stearate | 6 | 6 |
| | Retention Layer Weight | 600 | 600 |
| | Total Bilayer Tablet | 972 | 972 |

TABLE 13

Dissolution of Lot 013 (Glyceryl behenate) vs Lot 014 (Lubritab)

| Time (h) | Lot 013 -14 kP-Glyceryl behenate 888 | Lot 014-14 kP-Hydrogenated vegetable oil (Lubritab) |
|---|---|---|
| 0.5 | 4 | 1 |
| 1 | 8 | 3 |
| 2 | 18 | 11 |
| 4 | 36 | 31 |
| 6 | 51 | 52 |
| 8 | 63 | 70 |
| 12 | 82 | 96 |
| 16 | 95 | 103 |
| 20 | 101 | 104 |
| 24 | 103 | 105 |

2.4. Influence of Hypromellose Polymer Concentration on Apremilast Release

The influence of viscosity grades of hypromellose polymer on Apremilast drug release rate were investigated. Three formulations composited same compositions in roller compaction potion and in retention layer. The extra-granule excipients are composed of a consistent amount of Glyceryl behenate and total amount of Hypromellose, but different ratio of Hypromellose viscosity 4,000 mPa·S to Hypromellose viscosity 100 mPa·S. The Hypromellose 4,000 mPa·S: 100 mPa·S ratio was 100:0 for Lot 013, 0:100 for Lot 015 and 50:50 for Lot 016 in three formulations, respectively. The dissolutions results indicated that drug release can be slowed down with increasing hypromellose viscosity 4,000 mPa·S amount in the formulation. Lot 015 can provide sustained drug release profile for 12 hours, as for Lot 013 and Lot 016 have similar dissolution profiles, which provide sustained drug release profile for 16 hours by matrix diffusion and erosion process. The API layer completely disappeared after 100% API was released, which indicated that the drug release is controlled by a matrix erosion mechanism.

The bilayer tablets were produced by the same manufacturing process as described in Example 2.3.

TABLE 14

Formulations of Lot 013, LOT 015 and LOT 016

| | | Lot No. | | |
|---|---|---|---|---|
| | MATERIAL DESCRIPTION | 013 mg/Tab | 015 mg/Tab | 016 mg/Tab |
| API layer Roller Compacted Granules | Apremilast Form B | 60 | 60 | 60 |
| | Poloxamer | 10 | 10 | 10 |
| | Lactose Anhydrous Impalpable | 50 | 50 | 50 |
| | Microcrystalline cellulose | 90 | 90 | 90 |
| | Hydroxypropyl Cellulose | 76 | 76 | 76 |
| | Colloidal Silicon Dioxide | 4 | 4 | 4 |
| | Magnesium Stearate | 4 | 4 | 4 |
| | | 294 | 294 | 294 |
| API layer Extra-granular | Glyceryl behenate | 37 | 37 | 37 |
| | Hypromellose viscosity 4,000 mPa·S | 37 | — | 18.5 |
| | Hypromellose (Hypromellose viscosity 100 mPa·S DC2) | — | 37 | 18.5 |
| | Colloidal Silicon Dioxide | 4 | 4 | 4 |
| | | 240 | 203 | 221.5 |
| | Total API layer | 372 | 372 | 372 |
| | Cellulose Acetate CA-398-10 NF | 89.4 | 89.4 | 89.4 |

TABLE 14-continued

Formulations of Lot 013, LOT 015 and LOT 016

|  | Lot No.<br>MATERIAL<br>DESCRIPTION | 013<br>mg/Tab | 015<br>mg/Tab | 016<br>mg/Tab |
|---|---|---|---|---|
| Retention<br>Layer | Polyethylene oxide<br>(Poly(ethylene oxide)<br>7,000,000 molecular weight) | 252 | 252 | 252 |
|  | Hypromellose (Hypromellose<br>viscosity 100 mPa · S DC2) | 162 | 162 | 162 |
|  | Citric Acid | 36 | 36 | 36 |
|  | Sodium Bicarbonate | 54 | 54 | 54 |
|  | Colorant | 0.6 | 0.6 | 0.6 |
|  | Magnesium Stearate | 6 | 6 | 6 |
|  | Retention Layer Weight | 600 | 600 | 600 |
|  | Total Bilayer Tablet | 972 | 972 | 972 |

TABLE 15

Dissolution Data in 900 mL pH 4.5, 50 rpm Acetate buffer with 2% Tween 80 at 37° C. by Paddle, 75 rpm

| Time (h) | Lot 013 -10%<br>Hypromellose<br>4000 mPa · S | 015-10%<br>Hypromellose<br>100 mPa · S | Lot 016 - 5% Hypromellose<br>4000 mPa · S -5%<br>Hypromellose 100 mPa · S |
|---|---|---|---|
| 0.5 | 4 | 5 | 4 |
| 1 | 8 | 12 | 7 |
| 2 | 18 | 27 | 17 |
| 4 | 36 | 55 | 37 |
| 6 | 51 | 78 | 55 |
| 8 | 63 | 94 | 69 |
| 12 | 82 | 105 | 90 |
| 16 | 95 | 106 | 99 |
| 20 | 101 | 107 | 101 |
| 24 | 103 | 108 | 102 |

2.5 Influence of the Granulation Process on Drug Release 2.5.1 Influence of Roller Compaction Process on Drug Release In the Roller compaction process, some ingredients are added as Intra-granules to increase the particle density, hence increasing flowability and compressibility, ex API and dry binder agents etc., and some of ingredients are added as Extra-granules in final blending process, ex lubricant and glidant etc. For a drug release controlling agent either can be added into roller compaction process or added as Extra granule by a dry blending process. But roller compaction process may affect the characteristic of the drug release controlling agent, therefore affect drug release process. In this study, 017 and 018 share the same formulation and process (roller compaction granulation followed by tablet compression). The only difference is that Hypromellose viscosity 4,000 mPa·S was added extra-granularly in Lot 017 and intra-granularly in Lot 018. Dissolution data demonstrate that tablets with intra-granular hypromellose resulted in slower drug release with smaller inter-tablet % RSD than tablets with extra-granular Hypromellose. This is attributed to the roller compaction process making denser granules than the dry lending process, therefore providing a slower drug release profile.

2.5.2 Influence of Fluid Bed Process on Drug Release

As comparing to roller compaction dry granulation process, fluid bed granulation is a wet granulation process, which produces lower density granules. The different granule characteristics may affect tablet compression and drug release rate. The influence of the granulation process was investigated with Lot 018 and Lot 019, having similar formulation with Hypromellose viscosity 4,000 mPa·S, which incorporated intra-granularly, but Lot 019 was granulated by fluid bed granulation process. Tablets from lot 019 and lot 127 were compressed into the same hardness. The dissolution data showed that Lot 018 and Lot 019 had similar dissolution profiles. This indicated that the granulation processes had no significant influence on the drug release in current case. The results suggested that fluid bed granulation technology can be used for API Apremilast Form B, which is stable with liquids.

TABLE 32

Formulation composition of Apremilast Bilayer Tablet by roller compaction lot 017 and 018

|  |  | Bilayer Tablet Lot No. | |
|---|---|---|---|
| Process | MATERIAL DESCRIPTION | 017<br>Roller<br>Compaction:<br>hypromellose<br>extra-granular<br>mg/Tab | 018<br>Roller<br>Compaction:<br>hypromellose<br>intra-granular<br>mg/Tab |
| API layer | Apremilast Form B | 60 | 60 |
| Roller | Hypromellose viscosity 4,000 mPa · S | — | 37 |
| Compacted | Poloxamer | 10 | 10 |
| Granules | Lactose Anhydrous Impalpable | 50 | 50 |
|  | Microcrystalline cellulose | 90 | 90 |
|  | Hydroxypropyl Cellulose | 76 | 76 |
|  | Colloidal Silicon Dioxide | 4 | 4 |

TABLE 32-continued

Formulation composition of Apremilast Bilayer Tablet by roller compaction lot 017 and 018

| | | Bilayer Tablet Lot No. | |
|---|---|---|---|
| | | 017 Roller Compaction: hypromellose extra-granular mg/Tab | 018 Roller Compaction: hypromellose intra-granular mg/Tab |
| Process | MATERIAL DESCRIPTION | | |
| Extra-granular | Magnesium Stearate | 4 | 4 |
| | Glyceryl behenate | 37 | 37 |
| | Hypromellose viscosity 4,000 mPa · S | 37 | — |
| | Colloidal Silicon Dioxide | 4 | 4 |
| Retention Layer Lot NS002-120 | Total API layer | 372 | 372 |
| | Cellulose Acetate | 50 | 50 |
| | Poly(ethylene oxide) 7,000,000 molecular weight | 180 | 180 |
| | Hypromellose viscosity 100 mPa · S | 234 | 234 |
| | Citric Acid | 36 | 36 |
| | Sodium Bicarbonate | 54 | 54 |
| | Colorant (D&C YELLOW #10 Aluminum Lake) | 0.5 | 0.5 |
| | Lactose monohydrate 11SD | 39.5 | 39.5 |
| | Magnesium Stearate | 6 | 6 |
| | Retention Layer Weight | 600 | 600 |
| | Total Bilayer Tablet | 972 | 972 |

TABLE 33

Formulation composition of Apremilast Bilayer Tablets: Flued bed granulation lot 019 vs Roller compaction Lot 018

| | | 019-hypromellose intra-granular (Fluid Bed) | | | 018-hypromellose intra-granular (Roller Compaction) | | |
|---|---|---|---|---|---|---|---|
| Process | Material | mg/Tab | % w/w | Material | mg/Tab | % w/w | |
| API layer | Apremilast Form B | 60 | 16.13 | Apremilast Form B | 60 | 16.13 | |
| | Poloxamer | 10 | 2.69 | Poloxamer | 10 | 2.69 | |
| | Lactose Anhydrous Impalpable | 50 | 13.44 | Lactose Anhydrous Impalpable | 50 | 13.44 | |
| | Microcrystalline cellulose | 60 | 16.13 | Microcrystalline cellulose | 90 | 24.19 | |
| | Hypromellose viscosity 4,000 mPa · S | 37 | 9.95 | Hypromellose viscosity 4,000 mPa · S | 37 | 9.95 | |
| | Hydroxypropyl Cellulose | 76 | 20.43 | Hydroxypropyl Cellulose | 76 | 20.43 | |
| | Hypromellose viscosity 6 mPa · S | 8 | 2.15 | 0 | 0 | 0 | |
| | Colloidal Silicon Dioxide | 0 | 0 | Colloidal Silicon Dioxide | 4 | 1.08 | |
| | Magnesium Stearate | 0 | 0 | Magnesium Stearate | 4 | 1.08 | |
| Extra-granular | Microcrystalline cellulose | 30 | 8.06 | 0 | 0 | 0 | |
| | Glyceryl behenate | 37 | 9.95 | Glyceryl behenate | 37 | 9.95 | |
| | Colloidal Silicon Dioxide | 4 | 1.08 | Colloidal Silicon Dioxide | 4 | 1.08 | |
| Retention Layer Dry Blending | Total API layer | 372 | 100.00 | Total API layer | 372 | 100.00 | |
| | Cellulose Acetate | 33.3 | 8.33 | Cellulose Acetate | 50 | 8.33 | |
| | Poly(ethylene oxide) 7,000,000 molecular weight | 120 | 30 | Poly(ethylene oxide) 7,000,000 molecular weight | 180 | 30.00 | |
| | Hypromellose viscosity 100 mPa · S | 156 | 39 | Hypromellose viscosity 100 mPa · S | 234 | 39.00 | |

TABLE 33-continued

Formulation composition of Apremilast Bilayer Tablets: Flued bed granulation lot 019 vs Roller compaction Lot 018

| Process | 019-hypromellose intra-granular (Fluid Bed) | | | 018-hypromellose intra-granular (Roller Compaction) | | |
|---|---|---|---|---|---|---|
| | Material | mg/Tab | % w/w | Material | mg/Tab | % w/w |
| | Citric Acid | 24 | 6 | Citric Acid | 36 | 6.00 |
| | Sodium Bicarbonate | 36 | 9 | Sodium Bicarbonate | 54 | 9.00 |
| | Colorant (D&C YELLOW #10 Aluminum Lake) | 0.3 | 0.08 | Colorant (D&C YELLOW #10 Aluminum Lake) | 0.5 | 0.08 |
| | Lactose monohydrate 11SD | 26.3 | 6.58 | Lactose monohydrate 11SD | 39.5 | 6.58 |
| | Magnesium Stearate | 4 | 1 | Magnesium Stearate | 6 | 1.00 |
| | Retention Layer Weight | 399.9 | 100 | Retention Layer Weight | 600 | 100 |
| Total Bilayer Table | Oval | 771.9 | | | 972 | |

TABLE 34

Dissolution of Lot 017, 019, and 018.

| Time (h) | Lot 017 - 60 mg RC hypromellose Extra-granular % Diss | Lot 018- 60 mg RC hypromellose Intra-granular % Diss | Lot 019-60 mg FB Granulation % Diss |
|---|---|---|---|
| 0 | 0 | 0 | 0 |
| 0.5 | 2 | 2 | 3 |
| 1 | 6 | 5 | 6 |
| 2 | 15 | 12 | 14 |
| 4 | 36 | 28 | 30 |
| 6 | 56 | 43 | 45 |
| 8 | 74 | 58 | 60 |
| 12 | 95 | 80 | 84 |
| 16 | 99 | 93 | 98 |
| 20 | 100 | 96 | 103 |
| 24 | 100 | 96 | 104 |

Dissolution method: 900 mL pH 4.5, 50 mM Acetate buffer with 2% Tween 80 at 37° C., Paddle speed (100 rpm), with large helix sinker The granulations are characterized by the tests of particle size distribution, bulk density and tapped density to evaluate the influence of the granulation process on physical characteristics of the granulations. The data shown that granules (Lot 017 and Lot 018) made by roller compaction process have higher density, hence better flowability than granules made by fluid bed granulation process (Table 35). Lot 017 and Lot 018 have similar particle sizes with a wide particle size distribution, mainly retained on pan to 500 µm meshes. Lot 019 has small but narrow particle size distribution than Lot 017 and Lot 018. This suggested that fluid bed granulation process can produce narrower particle size distribution than roller compaction process.

TABLE 35

Data of the Bulk/Tapped Density and Hausner Ratio

| API layer Blend | Lot 017 - Roller Compactor | Lot 018-RC hypromellose Intra- Granular | Lot 019- FB Granulation |
|---|---|---|---|
| Bulk density, g/mL | 0.625 | 0.490 | 0.209 |
| Tap density, g/mL | 0.689 | 0.590 | 0.258 |
| Hausner Ratio | 1.10 | 1.20 | 1.23 |

2.6. Influence of Floating-Systems on floating Capability

The retention layer is composed of: (a) Gel forming agent Hypromellose viscosity 100 mPa·S and Poly(ethylene oxide) 7,000,000 molecular weight; (b) Gas generating agent, Sodium Bicarbonate and Citric Acid to form $CO_2$; (c) Low density, water insoluble floating agent and matrix former Cellulose Acetate; and (d) hydrophilic filler Lactose monohydrate 11SD. The current innovated gastro retentive system (GRS) combines two systems together to retain the tablet in stomach for a prolonged time. 1.) Swelling matrix system: This system is formed by some hydrophilic polymers ex Polyethylene oxide and/or hydrophobic low-density polymers ex Cellulose Acetate, which was combined with the hydrophilic polymers together to form a matrix system in current case. After in contact with water, hydrophilic polymers will swell and expand to form low density matrix layer, hence generate buoyancy. 2) Gas-generating systems: This system is formed by gas generating agents to form $CO_2$, ex Sodium Bicarbonate react with Citric Acid to generate $CO_2$, which form the porosities in the matrix to make the matrix layer less dense, hence floating on the on the gastric fluids.

Retention layer of Formulation Lot 017 was a combination of Swelling/expanding matrix floating system and Gas-generating systems. In this example, bilayer tablets were prepared with the same API layer as in Lot 017 formulation, but different formulations for retention layer, in which Gas-generating systems were removed. The formulations were comprised of different ratios of polymer Cellulose Acetate and Polyethylene oxide (7,000,000 molecular weight).

By comparing Lot 020A with Lot 017, it was found that retention layer without Gas-generating systems did not influence the floating lag time, floating time, and dissolution profiles. While comparing Lot 020A (Cellulose acetate 23.33%) with lot 020C (replacing cellulose acetate with lactose monohydrate) and lot 020D (replacing cellulose acetate with Polyethylene oxide), dissolution profiles were similar but lag time increased for the two formulations without cellulose acetate. Surprisingly, inclusion of cellulose acetate in the retention layer reduces floating lag time for the bilayer tablets.

However, retention layer replacing Polyethylene oxide with Cellulose Acetate (CA) in the formulation (Lot 020B), resulted in shorter total floating time (retention layer disintegrated within 15 hours) and faster dissolution. This indicated that the compared to Cellulose Acetate, Polyethylene oxide is more efficient to form a stronger matrix layer. This is attributed to Polyethylene oxide as a hydrophilic polymer with high molecular weight and viscosity (MW 7000,000, 7500-10,000 mPa·S). Therefore, Polyethylene oxide played a key role to form a stronger retention layer for a longer floating time, hence maintained API layer floated in gastric fluid to provide for a prolonged drug release. While surprisingly, the formulation of Lot 017 with about 23% Cellulose Acetate generated a shortest floating lag time, the tablets floated immediately and floating for more than 24 hours. This is attributed to the Cellulose Acetate is a hydrophobic polymer with low density, which does not need a hydrating/swelling process to generate buoyancy, but the low-density characteristic helps the tablet quickly float on the surface of the liquid media, and will not be eroded by liquids. Therefore the floating capability of the retention layer can be adjusted by change of the combination ratio of the two polymers (CA and Polyethylene oxide) in the retention layer.

The floating capability of the retention layer can be adjusted by change of the combination ratio of two polymers in the retention layer.

TABLE 41

Formulation composition of Apremilast lot NS002-020A/B/C/D and Lot 017.

| Process | MATERIAL DESCRIPTION | 020A mg/Tab | 020B mg/Tab | 020C mg/Tab | 020D mg/Tab | 017 mg/Tab |
|---|---|---|---|---|---|---|
| API layer Roller Compacted Granules LotNS002-110A | Apremilast Form B | 60 | 60 | 60 | 60 | 60 |
| | Poloxamer | 10 | 10 | 10 | 10 | 10 |
| | Lactose Anhydrous Impalpable | 50 | 50 | 50 | 50 | 50 |
| | Microcrystalline cellulose | 90 | 90 | 90 | 90 | 90 |
| | Hydroxypropyl Cellulose | 76 | 76 | 76 | 76 | 76 |
| | Colloidal Silicon Dioxide | 4 | 4 | 4 | 4 | 4 |
| | Magnesium Stearate | 4 | 4 | 4 | 4 | 4 |
| API layer Extra-granular | Glyceryl behenate | 37 | 37 | 37 | 37 | 37 |
| | Hypromellose viscosity 4,000 mPa · S | 37 | 37 | 37 | 37 | 37 |
| | Colloidal Silicon Dioxide | 4 | 4 | 4 | 4 | 4 |
| | Total API layer | 372 | 372 | 372 | 372 | 372 |
| Floating/ Retention Layer | Cellulose Acetate | 140 | 320 | — | — | 89.4 |
| | Polyethylene oxide (Poly(ethylene oxide) 7,000,000 molecular weight) | 180 | — | 180 | 320 | 252 |
| | Hypromellose (Hypromellose viscosity 100 mPa · S) | 234 | 234 | 234 | 234 | 162 |
| | Colorant | 0.5 | 0.5 | 0.5 | 0.5 | 0.6 |
| | Lactose monohydrate | 39.5 | 39.5 | 179.5 | 39.5 | — |
| | Magnesium Stearate | 6 | 6 | 6 | 6 | 6 |
| | Citric Acid | — | — | — | — | 36 |
| | Sodium Bicarbonate | — | — | — | — | 54 |
| | Retention Layer Weight | 600 | 600 | 600 | 600 | 600 |
| | Total Bilayer Tablet | 972 | 972 | 972 | 972 | 972 |

TABLE 42

Dissolution Data for Apremilast ER Bilayer Tablet 60 mg Lot 020 and Lot 017.

| Time point: hr | Lot 020A - 14 kP (No Effervescent Agent) % Diss | Lot 020B - 14 kP (No Effervescent Agent No Polyox) % Diss | Lot 020C - 14 kP (No Effervescent Agent No CA, More Lactose) % Diss | Lot 020D - 14 kP (No Effervescent Agent No CA, More Polyox) % Diss | Lot 017 - 14 kP (Effervescent, CA, Polyox) % Diss |
|---|---|---|---|---|---|
| 0 | 0 | 0 | 0 | 0 | 0 |
| 0.5 | 2 | 2 | 2 | 2 | 2 |
| 1 | 5 | 7 | 6 | 5 | 6 |
| 2 | 13 | 21 | 16 | 15 | 15 |
| 4 | 31 | 47 | 36 | 33 | 36 |
| 6 | 50 | 69 | 55 | 50 | 56 |
| 8 | 66 | 85 | 73 | 66 | 74 |
| 12 | 91 | 101 | 97 | 88 | 95 |

TABLE 42-continued

Dissolution Data for Apremilast ER Bilayer Tablet 60 mg Lot 020 and Lot 017.

| Time point: hr | Lot 020A - 14 kP (No Effervescent Agent) % Diss | Lot 020B - 14 kP (No Effervescent Agent No Polyox) % Diss | Lot 020C - 14 kP (No Effervescent Agent No CA, More Lactose) % Diss | Lot 020D - 14 kP (No Effervescent Agent No CA, More Polyox) % Diss | Lot 017 - 14 kP (Effervescent, CA, Polyox) % Diss |
|---|---|---|---|---|---|
| 16 | 103 | 105 | 104 | 98 | 99 |
| 20 | 106 | 105 | 105 | 102 | 100 |
| 24 | 108 | 105 | 106 | 104 | 100 |
| Floating Behavior | Float immediately, still floating after 24 hours | Float Immediately, but retention layer disintegrated within 15 hours | Float in 10 min; although retention layer was still floating at 24 h, it showed obvious erosion | Float in 10 min, still floating after 24 hours | Float immediately, still floating after 24 hours |

Dissolution method: 900 mL pH 4.5 50 mM sodium acetate buffer with 2% Tween 80 at 37° C. Paddle 100 rpm

Example 3. Apremilast (Amorphous) Bilayer Gastroretentive ER Tablets 3.1 Influence of Apremilast Polymorphism (Crystal Form B Vs Amorphous)

The different physical properties exhibited by polymorphs affect important pharmaceutical parameters such as storage, stability, compressibility, density and dissolution rates. Stability differences may result from changes in chemical reactivity, mechanical changes (e.g., tablets crumble on storage as a kinetically favored crystalline form converts to thermodynamically more stable crystalline form) or both (e.g., tablets of one polymorph are more susceptible to breakdown at high humidity).

An amorphous form generally provides better solubility and bioavailability than the crystalline form and may be useful for formulations which can have better solubility, and compressibility etc. which are important for formulation and product manufacturing. The API physicochemical data indicated that: 1) Crystalline Form B and amorphous form were stable after exposing to different stress test conditions; 2) Apremilast amorphous form were stable after 6 months under exposing to different stress test conditions, and under both long term conditions 25° C./60% RH and accelerated conditions 40° C./75% RH; 3) Solubility is not pH dependent but higher solubility results were obtained for Apremilast amorphous form than Form B.

Formulations with Apremilast form B and Apremilast amorphous form were developed with a same composition and same manufacturing process, respectively with bilayer tablet technology (Bilayer Tablet Compression: Elizabeth bilayer tablet press EP200L. The drug release rates were tested in 900 mL pH 4.5, 50 mM Acetate buffer with 2% Tween 80 at 37° C., Paddle speed (75 rpm vs 100 rpm), with large helix sinker.

The dissolutions results indicated that the gastroretension sustained release formulation with Apremilast amorphous form and Apremilast Form B were successfully developed, Apremilast physical characteristics have significant influence on drug release rate. The formulation of lot 017 (Form B) provided a significant faster drug rate (t50 is about 6 hrs) than lot 021 (Amorphous Form)(t50 is about 12 hrs) with paddle speed 100 rpm. This attributed to Apremilast amorphous form has significant larger particles (d90=22 μm) than Apremilast Form B (d90=8 μm)), even Apremilast amorphous has relatively higher solubility (0.224 mg/ml) than Apremilast amorphous (0.020 mg/ml) in pH4.5 buffer. The dissolution data also indicated that increasing paddle speed resulted in a faster drug release rate for the both of formulations composed by Apremilast form B and Apremilast amorphous form, respectively.

TABLE 43

Formulation composition of Apremilast lot 017 and 021.

| Process | MATERIAL DESCRIPTION | 017 (Form B) mg/Tab | 021 (Amorphous) mg/Tab |
|---|---|---|---|
| API layer | Apremilast Form B | 60 | — |
| Roller Compacted | Apremilast Amorphous | — | 60 |
| Granules | Poloxamer | 10 | 10 |
| NS002-119 | Lactose Anhydrous Impalpable | 50 | 50 |
| | Microcrystalline cellulose | 90 | 90 |
| | Hydroxypropyl Cellulose | 76 | 76 |
| | Colloidal Silicon Dioxide | 4 | 4 |
| | Magnesium Stearate | 4 | 4 |
| Extra-granular | Glyceryl behenate | 37 | 37 |
| | Hypromellose viscosity 4,000 mPa · S | 37 | 37 |
| | Colloidal Silicon Dioxide | 4 | 4 |
| | Total API layer | 372 | 372 |
| Swelling Layer | Hypromellose viscosity 100 mPa · S | 234 | 234 |
| Lot NS002-120 | Poly(ethylene oxide) 7,000,000 molecular weight | 180 | 180 |
| | Sodium Bicarbonate | 54 | 54 |
| | Citric Acid | 36 | 36 |
| | Cellulose Acetate | 50 | 50 |

TABLE 43-continued

Formulation composition of Apremilast lot 017 and 021.

| Process | MATERIAL DESCRIPTION | 017 (Form B) mg/Tab | 021 (Amorphous) mg/Tab |
|---|---|---|---|
| | Lactose monohydrate 11SD | 39.5 | 39.5 |
| | Magnesium Stearate | 6 | 6 |
| | Colorant (D&C YELLOW #10 Aluminum Lake) | 0.5 | 0.5 |
| | Retention Layer Weight | 600 | 600 |
| | Total Bilayer Tablet | 972 | 972 |

Bilayer Tablet Compression: Elizabeth bilayer tablet press EP200L

TABLE 44

Dissolution of Lot 017 and 021

| Time (h) | Lot 017 -_100 rpm-APT-Form B | Lot 017 -_75 rpm-APT-Form B | Lot 021 -_100 rpm-Amorphous | Lot 021 -_75 rpm-Amorphous |
|---|---|---|---|---|
| 0.5 | 1.9 | 1.1 | 1.5 | 1.3 |
| 1 | 5.6 | 3.6 | 3 | 2.7 |
| 2 | 15.1 | 10.5 | 6.8 | 6.3 |
| 4 | 35.6 | 25.5 | 15.9 | 14.6 |
| 6 | 56.1 | 41.4 | 25.8 | 23.7 |
| 8 | 74.2 | 57.3 | 35.1 | 32.4 |
| 12 | 95.2 | 81.2 | 52.5 | 48.7 |
| 16 | 99.2 | 92.8 | 67.1 | 61.5 |
| 20 | 99.5 | 94.5 | 77.5 | 70.8 |
| 24 | 99.5 | 93.2 | 84.4 | 77 |
| Floating lag time | 0 min | 5 min | 0 min | 5 min |
| Total Floating time | >24 hours | >24 hours | >24 hours | >24 hours |

900 mL pH 4.5, 50 mM Acetate buffer with 2% Tween 80 at 37° C., Paddle speed (75 rpm vs 100 rpm), with large helix sinker The swelling and floating capabilities of Apremilast bilayer tablets were evaluated in purified water at 37° C. The tablet length, width and thickness were measured from time zero, 0.5 hour, 1 hour, 2 hour, 4 hour, 8 hour, 12 hours and 24 hours during the tablets were floating in the medium. The results showed that following 30 minutes to 1 hour hydration, the bilayer tablets were quickly swelling and expanding to a significant larger size than their original size at time zero. The tablet length increased about 12% to about 20 mm in 30 minutes and increased about 50% in 8 hours and about 84% in 24 hours. The tablet width increased about 16% to about 11 mm in 30 minutes and about 40% in 8 hours and about 55% in 24 hours. The tablet thickness quickly increased about 60% to about 12 mm in 30 minutes, and then increased about 70% in 4 hours and about 95% in 24 hours. The tablets were floating in the medium for at least 24 hours. The results suggest that the bilayer tablets displayed fast swelling in the 30 to 60 minutes. All three dimensions continued to increase over the period of 24 hours and tablets were still floating at 24 h.

3.2 Influence of Glyceryl Behenate on Dissolution

Figure 2:
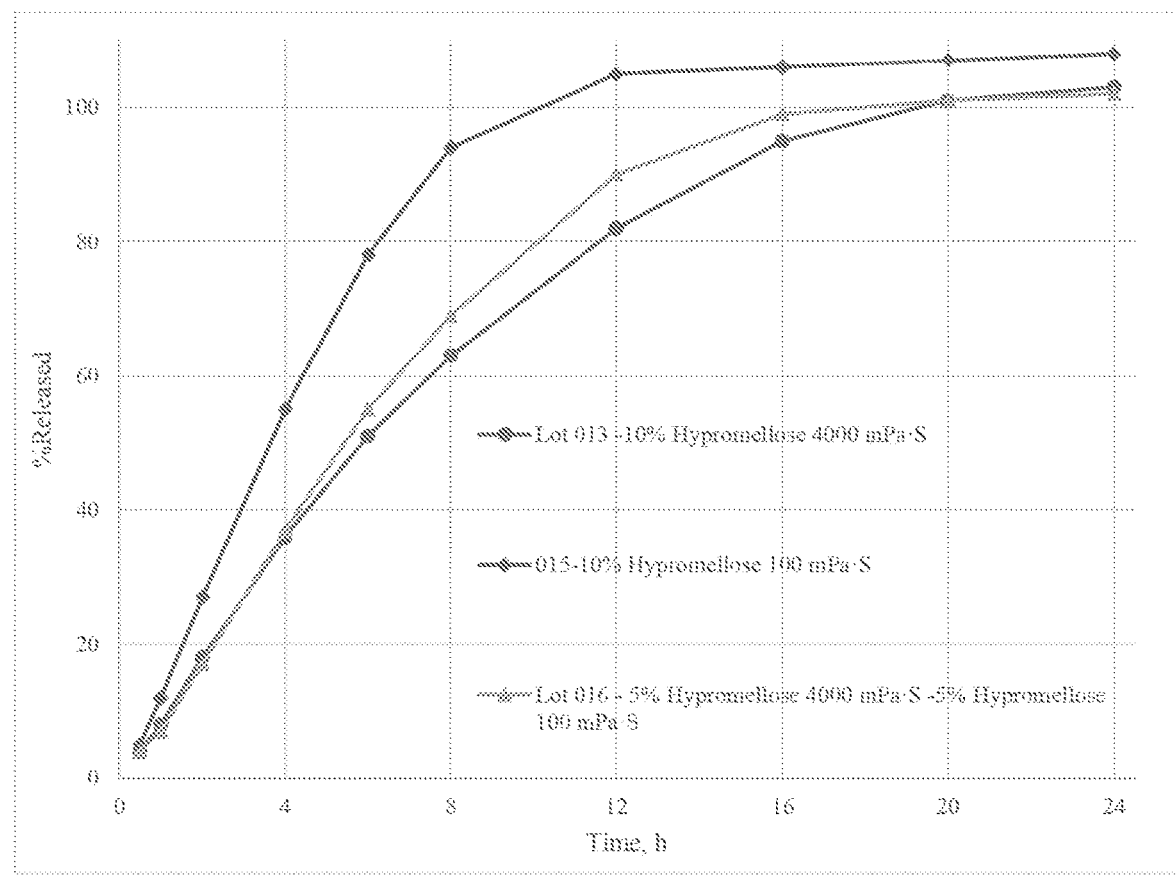
FIG. 2 shows the effect of hypromellose grades/viscosity on dissolution of different apremilast ER tablets in 900 mL pH 4.5, 50 rpm Acetate buffer with 2% Tween 80 at 37° C. by Paddle, 75 rpm
Figure 3:
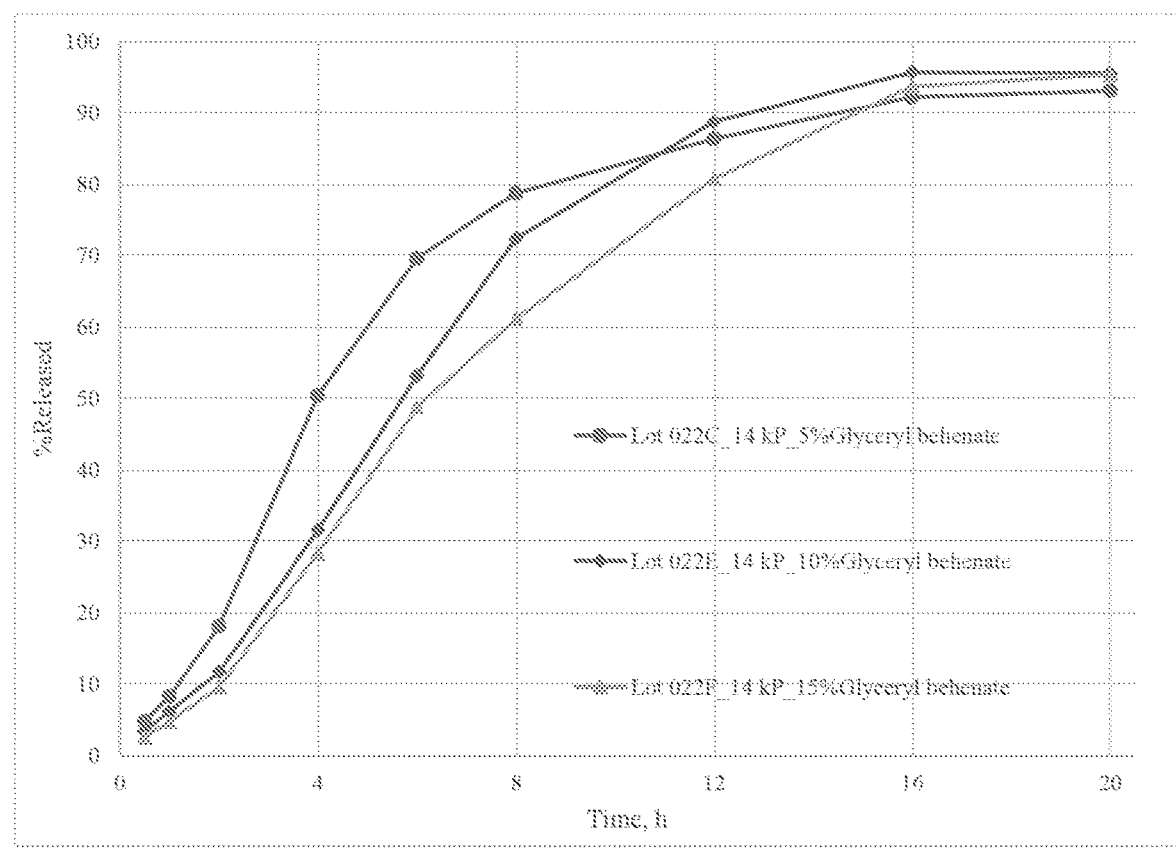
FIG. 3 shows the effect of glyceryl behenate on drug release for different apremilast ER bilayer tablets Lot NS002-137C/E/F.

In this case, three formulations were designed to increase the drug release rate based on adjusting the ratio of Glyceryl behenate in the formulation from 5% in the Lot 022C, 10% in Lot 022E and about 15% in the Lot 022F, respectively (Table 27). The dissolution data showed that all the three formulations can release more than 90% drug in 16 hours. The drug release was reduced with increasing the Glyceryl behenate. The results indicated that the drug delivery system can provide flexible drug release profiles from t50 at 4 hours to 6 hours, and t90 at 16 hours for all three formulations by a matrix erosion technology (Table 45, Tablet 46 and FIG. 2).

TABLE 45

Formulation composition of Apremilast lot 022C/E/F

| Process | MATERIAL DESCRIPTION | 022C (Amorphous) mg/Tab | 022E (Amorphous) mg/Tab | 022F (Amorphous) mg/Tab |
|---|---|---|---|---|
| API layer Roller Compacted Granules NS002-136 | Apremilast Amorphous | 60 | 60 | 60 |
| | Poloxamer | 10 | 10 | 10 |
| | Lactose Anhydrous Impalpable | 60 | 60 | 60 |
| | Microcrystalline cellulose | 90 | 90 | 90 |
| | Hydroxypropyl Cellulose | 20 | 20 | 20 |

TABLE 45-continued

Formulation composition of Apremilast lot 022C/E/F

| Process | MATERIAL DESCRIPTION | 022C (Amorphous) mg/Tab | 022E (Amorphous) mg/Tab | 022F (Amorphous) mg/Tab |
|---|---|---|---|---|
| | Sodium Starch glycolate | 5 | 5 | 5 |
| | Colloidal Silicon Dioxide | 2.5 | 2.5 | 2.5 |
| | Magnesium Stearate | 2.5 | 2.5 | 2.5 |
| | Intra-granular Total | 250 | 250 | 250 |
| Extra-granular | Glyceryl behenate | 13.5 | 27 | 45 |
| | Colloidal Silicon Dioxide | 2.5 | 3 | 3 |
| | Total API layer | 266 | 280 | 298 |
| Retention Layer Lot NS002-120 | Cellulose Acetate | 41.65 | 41.65 | 41.65 |
| | Poly(ethylene oxide) 7,000,000 molecular weight | 150 | 150 | 150 |
| | Hypromellose viscosity 100 mPa · S | 195 | 195 | 195 |
| | Citric Acid | 30 | 30 | 30 |
| | Sodium Bicarbonate | 45 | 45 | 45 |
| | Colorant (D&C YELLOW #10 Aluminum Lake) | 0.4 | 0.4 | 0.4 |
| | Lactose monohydrate 11SD | 32.9 | 32.9 | 32.9 |
| | Magnesium Stearate | 5 | 5 | 5 |
| | Retention Layer Weight | 500 | 500 | 500 |
| | Total Bilayer Tablet | 766 | 780 | 798 |

TABLE 46

Dissolution of Apremilast Amorphous ER Bilayer Tablets 60 mg Lot 022.

| Time (h) | Lot 022C_14 kP_5% Glyceryl behenate % Diss | Lot 022E_14 kP_10% Glyceryl behenate % Diss | Lot 022F_14 kP_15% Glyceryl behenate % Diss |
|---|---|---|---|
| 0.5 | 4.8 | 3.5 | 2.6 |
| 1 | 8.3 | 6.2 | 4.8 |
| 2 | 18.1 | 11.7 | 9.6 |
| 4 | 50.4 | 31.5 | 28.3 |
| 6 | 69.6 | 53.2 | 48.8 |
| 8 | 78.8 | 72.4 | 61.2 |
| 12 | 86.4 | 88.8 | 80.8 |
| 16 | 92.2 | 95.7 | 93.7 |
| 20 | 93.1 | 95.6 | 95.4 |

Dissolution method: 900 mL pH 4.5, 50 mM Acetate buffer with 2% Tween 80 at 37° C., Paddle speed 100 rpm with large helix sinker Example 4. Apremilast Bilayer Gastroretentive ER Tablets with Different Strengths The current innovated bilayer tablets were developed based on 60 mg Apremilast, but also were flexible for different strength tablets. In current case, Apremilast 30 mg and 100 mg were developed based on the 60 mg Apremilast formulation of Lot 023. The same API granules were used to formulate 30 mg and 100 mg strength tablets by adjusting intra-granular granule weight based on their ratios to 60 mg tablets. The extra-granular composition and retention layer was kept the same for all three strengths. The dissolution data shown that three different strength tablets had similar dissolution profiles. (f2>55 as compared to Lot 023 60 mg tablets).

TABLE 47

Formulation composition of Apremilast ER Bilayer Tablet 30 mg, 60 mg, and 100 mg.

| Process | MATERIAL DESCRIPTION | LOT 023_60 mg mg/Tab | LOT 024_100 mg mg/Tab | LOT 025_30 mg mg/Tab |
|---|---|---|---|---|
| API layer | Apremilast Form B | 60 | 100 | 30 |
| Roller Compacted Granules LotNS002-110A | Poloxamer | 10 | 16.7 | 5 |
| | Lactose Anhydrous Impalpable | 50 | 83.3 | 25 |
| | Microcrystalline cellulose | 90 | 150.0 | 45 |
| | Hydroxypropyl Cellulose | 76 | 126.7 | 38 |
| | Colloidal Silicon Dioxide | 4 | 6.7 | 2 |
| | Magnesium Stearate | 4 | 6.7 | 2 |
| | Intra-granular Weight | 294 | 490.1 | 147 |

TABLE 47-continued

Formulation composition of Apremilast ER Bilayer Tablet 30 mg, 60 mg, and 100 mg.

| Process | MATERIAL DESCRIPTION | LOT 023_60 mg mg/Tab | LOT 024_100 mg mg/Tab | LOT 025_30 mg mg/Tab |
|---|---|---|---|---|
| API layer Extra-granular | Glyceryl behenate | 37 | 37 | 37 |
| | Hypromellose viscosity 4,000 mPa · S | 37 | 37 | 37 |
| | Colloidal Silicon Dioxide | 4 | 4 | 4 |
| | Total API layer | 372 | 568 | 225 |
| Retention Layer | Cellulose Acetate CA-398-10 NF | 89.4 | 50 | 50 |
| | Polyethylene oxide (Poly(ethylene oxide) 7,000,000 molecular weight) | 252 | 180 | 180 |
| | Hypromellose (Hypromellose viscosity 100 mPa · S DC2) | 162 | 234 | 234 |
| | Citric Acid | 36 | 36 | 36 |
| | Sodium Bicarbonate | 54 | 54 | 54 |
| | Colorant | 0.6 | 0.5 | 0.5 |
| | Lactose monohydrate Supertab 11SD | — | 39.5 | 39.5 |
| | Magnesium Stearate | 6 | 6 | 6 |
| | Retention Layer Weight | 600 | 600 | 600 |
| | Total Bilayer Tablet | 972 | 1168 | 825 |

TABLE 48

Dissolution Data for Apremilast ER Bilayer Tablet 30 mg 60 mg and 100 mg

| Time point: hr | Lot 023 - _60 mg % Diss | Lot 024 - _100 mg % Diss | Lot 025 - 30 mg % Diss |
|---|---|---|---|
| 0 | 0 | 0 | 0 |
| 0.5 | 4 | 3 | 1 |
| 1 | 8 | 7 | 3 |
| 2 | 18 | 17 | 12 |
| 4 | 36 | 36 | 31 |
| 6 | 51 | 53 | 55 |
| 8 | 63 | 68 | 74 |
| 12 | 82 | 87 | 98 |
| 16 | 95 | 97 | 102 |
| 20 | 101 | 99 | 103 |
| 24 | 103 | 100 | 104 |

Example 5. Tofacitinib Gastroretentive ER Bilayer Tablet

The chemical name of tofacitinib citrate is 3-((3R,4R)-4-methyl-3-(methyl(7H-pyrrolo[2,3-d]pyrimidin-4 yl)amino)piperidin-1-yl)-3-oxopropanenitrile, 2-hydroxypropane-1,2,3-tricarboxylic acid corresponding to the molecular formula $C_{16}H_{20}N_6O$ and has a relative molecular mass 312.49 g/mol and the following structure:

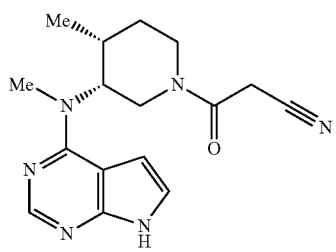

-continued

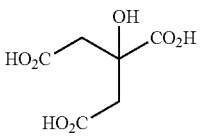

The chemical structure of tofacitinib has been adequately demonstrated by UV spectroscopy, infrared (IR) spectroscopy, 1H and 13C NMR spectroscopy, elemental analysis, mass spectrometry, and X-ray crystallography. The active substance is a white to off-white solid, slightly soluble in water (2.9 mg/mL) and non-hygroscopic. Tofacitinib contains two chiral centers at C3 and C4. The active substance is the enantiomer with absolute configuration (R) for both the C-3 and the C-4 positions. The overall stereochemistry of tofacitinib is therefore considered as critical and is assured by the quality of the starting materials and the route of synthesis design.

Polymorphism has been studied for the active substance. The crystalline citrate salt, Form A, has been the sole development form of the active substance used in all toxicology and clinical studies. The solubility Tofacitinib citrate is pH dependent, the solubility is decried with pH increasing. From FDA published data it can be seen that the aqueous solubility of Tofacitinib citrate is pH-dependent with higher solubility at low pH and drastically decreased solubility at pH above 3.9. The solubility data indicates that the highest solubility of Tofacitinib citrate is in pH 1.2 or 0.1N HCl medium. The pH dependent solubility can lead to pH-dependent in vivo drug release from sustained release matrices. Drug release varies as a function of movement through segments of the gastrointestinal tract with different pH. This can lead to inefficient drug delivery and large inter-subject variability, since pH in the gastrointestinal tract varies significantly between subjects. The Tofacitinib citrate gastric retention drug delivery system that would provide the highest bioavailability are very desirable because the drug active has highest solubility in the stomach.

TABLE 49

Solubility of Tofacitinib citrate in different pH media and water

| Solvent | Solubility @37° C., mg/mL for 6 hours | final pH observed |
|---|---|---|
| 0.1N HCl_solubility | 27.794 | 1.18 |
| pH 4.5_solubility | 4.568 | 4.50 |
| Water solubility | 2.9 | 4.90 |
| pH 6.8_solubility | 2.032 | 6.78 |

In this case, Tofacitinib gastric retention bilayer tablet is developed with a retention layer and an extended-release API layer. The retention layer will swell and float in stomach fluid, while the API layer provides controlled release drug profile. This dissolution results shown the gastric retention bilayer tablets provided extended drug release profiles. The drug release can be adjusted by changing concentration of Hypromellose viscosity 4,000 mPa·S in the API layer. The drug release was reduced with increasing amount of Hypromellose viscosity 4,000 mPa·S.

TABLE 50

Formulation composition of Tofacitinib ER Tablets 11 mg lot 026.

| | | Bilayer Tablet Lot No. | | | |
|---|---|---|---|---|---|
| | | 026A | | 026B | |
| Process | MATERIAL DESCRIPTION | mg/Tab | % w/w | mg/Tab | % w/w |
| API layer Fluid Bed Granules | Tofacitinib Citrate (11 mg base) | 17.77 | 7.11 | 17.77 | 7.11 |
| | Fumaric Acid, NF | 20.00 | 8.00 | 20.00 | 8.00 |
| | Citric acid (anhydrous) | 10.00 | 4.00 | 10.00 | 4.00 |
| | Microcrystalline Cellulose, NF | 14.00 | 5.60 | 14.00 | 5.60 |
| | Lactose Monohydrate, NF | 16.00 | 6.40 | 16.00 | 6.40 |
| | Compressible Sugar, NF | 45.23 | 18.09 | 45.23 | 18.09 |
| | Sodium Chloride, USP (milled) | 40.00 | 16.00 | 40.00 | 16.00 |
| | Sodium Starch glycolate | 4.00 | 1.60 | 4.00 | 1.60 |
| | Hypromellose viscosity 6 mPa · S | 6.00 | 2.40 | 6.00 | 2.40 |
| | Purified water | n/a | n/a | n/a | n/a |
| | Intra-granular Total | 173.00 | 69.2 | 173.00 | 69.2 |
| Extra-granular | Lactose Monohydrate | 47.0 | 18.8 | 34.5 | 13.8 |
| | Hypromellose viscosity 4,000 mPa · S | 25.0 | 10.0 | 37.5 | 15.0 |
| | Colloidal Silicon dioxide | 2.5 | 1.0 | 2.5 | 1.0 |
| | Magnesium Stearate | 2.5 | 1.0 | 2.5 | 1.0 |
| | Total API layer | 250 | 100 | 250 | 100 |
| Retention Layer Lot NS002-120 | Cellulose Acetate | 50 | 8.33 | 50 | 8.33 |
| | Poly(ethylene oxide) 7,000,000 molecular weight | 180 | 30.00 | 180 | 30.00 |
| | Hypromellose viscosity 100 mPa · S | 234 | 39.00 | 234 | 39.00 |
| | Citric Acid | 36 | 6.00 | 36 | 6.00 |
| | Sodium Bicarbonate | 54 | 9.00 | 54 | 9.00 |
| | Colorant (D&C YELLOW #10 Aluminum Lake) | 0.5 | 0.08 | 0.5 | 0.08 |
| | Lactose monohydrate | 39.5 | 6.58 | 39.5 | 6.58 |
| | Magnesium Stearate | 6 | 1.00 | 6 | 1.00 |
| | Retention Layer Weight | 600 | 100.0 | 600 | 100.0 |
| | Total Bilayer Tablet | 850 | | 850 | |

TABLE 51

Dissolution data of Tofacitinib ER Bilayer Tablets 11 mg Lot 026: effect of hypromellose on dissolution.

| Time point: hr | 026A (10% Hypromellose viscosity 4,000 mPa · S) % Diss | 026B (15% Hypromellose viscosity 4,000 mPa · S) % Diss |
|---|---|---|
| 0 | 0 | 0 |
| 0.25 | 18 | 15 |
| 0.5 | 29 | 25 |
| 0.75 | 38 | 32 |
| 1 | 45 | 39 |
| 2 | 64 | 57 |
| 4 | 85 | 79 |
| 6 | 92 | 90 |
| 8 | 95 | 94 |
| 10 | 96 | 96 |
| 12 | 96 | 96 |

Example 6. Relative Bioavailability Study of Apremilast Gastroretentive ER Bilayer Tablet The relative bioavailability of a single dose of Apremilast Gastroretentive ER Bilayer Tablet 60 mg relative to reference OTEZLA Apremilast immediate-release (IR) tablet 30 mg were performed. OTEZLA (Apremilast IR tablet 30 mg) was used as a reference.

TABLE 52

Test product Apremilast Gastroretentive ER Bilayer Tablet 60 mg

| Process | INGREDIENT | Qty per Tablet (%) |
|---|---|---|
| Drug Layer Intra-granular Fluid-bed granulation | Apremilast Form B | 6.8 |
| | Poloxamer (Kolliphor P188 Micro Geismar) | 0.5-1.5 |
| | Microcrystalline Cellulose (Pharmacel ®102) | 5-10 |
| | Hypromellose 100 mPa · S (Methocel ™ K100 Premium LVCR) | 5-15 |
| | Hypromellose (Pharmacoat 606) | 0.5-1.5 |
| Drug Layer Extra-granular | Microcrystalline Cellulose (Pharmacel ®102) | 1-3 |
| | Glyceryl dibehenate (Compritol 888 ATO) | 2.5-4.5 |
| | Colloidal silicon dioxide (Aerosil 200) | 0.1-0.6 |
| Retention Layer | Cellulose Acetate (Eastman ™ CA 398-10) | 4-6 |
| | Polyethylene oxide MW 7000 kDa (Sentry ™ Polyox WSR 303 LEO) | 16-20 |
| | Hypromellose 100 mPa · S (Methocel ™ K100LV DC 2) | 22-26 |
| | Citric Acid Anhydrous | 2.5-4.5 |
| | Sodium Bicarbonate anhydrous | 4-7 |
| | Lake pigment 6010 D&C Yellow #10 Aluminum lake | 0.05 |
| | Lactose monohydrate (Supertab ®11SD) | 3-5 |
| | Magnesium Stearate | 0.4-0.8 |
| Seal Coat | Amino Methacrylate Copolymer (Eudragit EPO) | 2-3 |
| | Polyethylene Glycol 6000 (Emprove ® essential) | 0.1-0.3 |
| | Talc | 0.5-2.0 |
| | Final Coated Tablet | 100 |

Preparation of Dosage Form
Step 1: Preparation of Retention Layer Blend
Excipients are weighed and passed through a cone mill.
Excipients are mixed in a bin blender.
This is the Retention layer blend for bilayer tablet compression.
Step 2: Preparation of Apremilast Layer Blend
Apremilast and intra-granular excipients are weighed and passed through a cone mill.
Apremilast and intra-granular excipients are mixed
Apremilast blend are granulated by roller compaction or fluid bed.
Extra-granular excipients are weighed and passed through a cone mill.
Extra-granular excipients and granules are mixed in a bin blender.
This is the Apremilast layer blend for bilayer tablet compression.
Step 3: Bilayer Tablet Compression
Bilayer tablet press is set up with the capsule-shape D-toolings.
Retention layer blend and Apremilast layer blend are loaded in the $1^{st}$ and $2^{nd}$ hopper respectively.
Retention layer ($1^{st}$ layer of the bilayer tablet) is adjusted to the target weight.
Bilayer tablet is compressed to the target weight and hardness.
Steps 4 Coating
Apremilast ER Tablets are Coated with a Film Coat.

This study was an open label, randomized, three-treatment, three-period, six-sequence, crossover, single-dose, relative bioavailability study of a single dose of Apremilast 60 mg Extended-Release Tablets (Test) under fasting and fed conditions and reference OTEZLA® (Apremilast) 30 mg Tablets (Reference) of Amgen given twice daily with 12-hour apart in healthy, adult, human subjects under fasting condition. During all study periods, blood samples to provide plasma for pharmacokinetic analysis was collected at periodic time points. The study results are provided in Table 53 and Table 54. The PK data indicated that under fed condition, the once daily Apremilast ER tablets 60 mg surprisingly provided promising PK data to have a similar Cmax and AUC 0-∞ to the twice daily OTEZLA (Apremilast immediate-release tablets 30 mg).

U.S. Pat. No. 9,532,977 B2, described a once daily Apremilast 75 mg ER, which had similar PK data of Cmax and AUC to the twice daily 30 mg IR tablets (Example 13). As compared to the once daily 75 mg ER, the dosage form of this patent document requires less API (no more than 60 mg Apremilast) to achieve bioequivalent AUC as in the case of the twice daily IR tablets (60 mg in total). Therefore, the dosage form of this patent document provides significant benefit to patient compliance, while achieving the efficacy and reducing potential side effects associated with a burst of release of API of IR tablets.

TABLE 53

PK data

| | Lntransformed Data Geometric Mean | | |
|---|---|---|---|
| | Test-Fasting | Test-Fed | Referece - Fasting |
| $C_{max}$(ng/mL) | 261.3221 | 491.7586 | 447.3335 |
| $AUC_{0-\infty}$(hr*ng/mL) | 3449.9383 | 6540.7149 | 6930.1839 |

TABLE 54

PK data

| Parameters | Test Fasting Vs Reference (A/C) Ratio (%) | Test Fed Vs Reference (B/C) Ratio (%) |
|---|---|---|
| $C_{max}$ | 58.42 | 109.93 |
| AUC 0-∞ | 49.78 | 94.38 |

It will be appreciated by persons skilled in the art that invention described herein are not limited to what has been particularly shown and described. Rather, the scope of the invention is defined by the claims which follow. It should further be understood that the above description is only representative of illustrative examples of embodiments. The description has not attempted to exhaustively enumerate all possible variations. The alternate embodiments may not have been presented for a specific component of the drug combination, or a step of the method, and may result from a different combination of described constituents, or that other un-described alternate embodiments may be available for a combination or method, is not to be considered a disclaimer of those alternate embodiments. It will be appreciated that many of those un-described embodiments are within the literal scope of the following claims, and others are equivalent.

What is claimed is:

1. An orally administrable extended release dosage form, comprising:
   (a) an active pharmaceutical ingredient (API) layer comprising a therapeutically effective amount of a first therapeutic agent, and one or more extended release agents providing extended release of the first therapeutic agent from the dosage form over a period of more than 8 hours in a medium, wherein the medium comprises 900 ml of 50 mM pH 4.5 acetate buffer with 2% Tween 80 at 37° C. with sinker in a standard USP rotating paddle apparatus having a paddle rotating speed of 100 rpm, wherein the first therapeutic agent is Tofacitinib or Apremilast, wherein the one or more extended release agents range from about 5% to about 50% by weight in the API layer;
   (b) a retention layer comprising one or more excipients, wherein the one or more excipients are selected to achieve the following:
      i. the dosage form stays afloat for more than 16 hours in the medium; and
      ii. a length and a width in the retention layer of the dosage form both remain equal or greater than 10 mm for more than 16 hours in un-stirred deionized sitting water or in the medium so that the dosage form remains bigger than the pyloric diameter of a human stomach;
   wherein the one or more excipients in the retention layer comprise a first hypromellose, polyethylene oxide and cellulose acetate, wherein the polyethylene oxide has an MW of no less than 1000 kDa, wherein the polyethylene oxide and the cellulose acetate in a ratio ranging from about 10:1 to about 1:1,
   wherein the API layer and the retention layer are in a ratio ranging from about 1:4 to about 2:1 by weight.

2. The dosage form of claim 1, further comprising a third layer comprising a therapeutically effective amount of a second therapeutic agent.

3. The dosage form of claim 1, further comprising a third layer for a second therapeutic agent, wherein the retention layer is sandwiched between the other two layers.

4. The dosage form of claim 1, wherein the first therapeutic agent is amorphous Apremilast.

5. The dosage form of any one of claim 1, wherein the one or more extended release agents in the API layer and the one or more excipients in the retention layer are selected to control the release of the first therapeutic agent in the medium such that
   (a) less than 10% of the first therapeutic agent is released within about 1 hour; and
   (b) from about 40% to about 60%, of the first therapeutic agent is release within about 8 hours,
   wherein the first therapeutic agent is Apremilast.

6. The dosage form of claim 1, wherein more than 90% of the first therapeutic agent is released in 24 hours in the medium.

7. The dosage form of claim 1, wherein the one or more extended release agents in the API layer and the one or more excipients in the retention layer are selected to control the release of the first therapeutic agent ranging from about 40 mg to about 80 mg such that the dosage form administered once a day (QD) with food provides an area under curve (AUC) of the first therapeutic agent ranging from about 80% to about 125% of the AUC of the first therapeutic agent in a daily dosage of about 60 mg administered twice a day (BID) as an immediate release formulation, wherein the first therapeutic agent is Apremilast.

8. The dosage form of claim 1, wherein the one or more extended release agents in the API layer and the one or more excipients in the retention layer are selected to control the release of the first therapeutic agent ranging from about 8 mg to about 15 mg such that the dosage form administered QD with food provides an area under curve (AUC) of the first therapeutic agent ranging from about 80% to about 125% of the AUC of the first therapeutic agent in a daily dosage of about 10 mg administered BID as an immediate release formulation, wherein the first therapeutic agent is tofacitinib.

9. The dosage form of claim 1, wherein the one or more extended release agents in the API layer and the one or more excipients in the retention layer are selected to control the release of the first therapeutic agent ranging from about 15 mg to about 25 mg such that the dosage form administered QD with food provides an area under curve (AUC) of the first therapeutic agent ranging from about 70% to about 125% of the AUC of the first therapeutic agent in a daily dosage of about 20 mg administered BID as an immediate release formulation, wherein the first therapeutic agent is tofacitinib.

10. The dosage form of claim 1, wherein the one or more extended release agents in the API layer comprise one or more of ethylcellulose, methylcellulose, hydroxypropyl cellulose, hypromellose, hypromellose phthalate, cellulose acetate, cellulose acetate phthalate, polyvinylalcohol, polyvinylacetate, polyacrylate, polymethacrylate, wax, and glyceryl ester of a fatty acid.

11. The dosage form of claim 10, wherein the one or more extended release agents comprise the glyceryl ester of a fatty acid, which is glyceryl behenate, wherein the glyceryl behenate comprises glyceryl dibehenate.

12. The dosage form of claim 1, wherein the one or more extended release agents comprise at least two types of hypromelloses, wherein one of the at least two types of hypromelloses has viscosity of higher than about 3,000 mPa·S and the other of the at least two types of hypromelloses has viscosity of lower than about 200 mPa·S.

13. The dosage form of claim 1, wherein the one or more excipients in the retention layer comprise low density agents selected from the group consisting of cellulose acetate, hydrogenated vegetable oil, glyceryl behenate, ethylcellulose, and wax.

14. The dosage form of claim 13, wherein the one or more excipients in the retention layer further comprise one or more swelling agent selected from the group consisting of hydroxypropyl cellulose, polyethylene oxide, carboxymethylcellulose, Croscarmellose Sodium, sodium starch glycolate, cross-linked povidone, and chitosan.

15. The dosage form of claim 1, wherein the polyethylene oxide and cellulose acetate are in a ratio ranging from about 6:1 to about 2:1.

16. The dosage form of claim 1, wherein the first hypromellose is in an amount ranging from about 5% to about 50% in the retention layer.

17. The dosage form of claim 1, wherein the retention layer further comprises an effervescent agent and an acid source, wherein the total weight of the effervescent agent and the acid source ranges from about 5% to about 20% in the retention layer.

18. The dosage form of claim 1, wherein the one or more extended release agents in the API layer and the one or more excipients in the retention layer are selected to control retention of the dosage form in the stomach such that the dosage form begins to float in 10 minutes and remains afloat for 24 hours in the medium.

19. The dosage form of claim 1, wherein the one or more excipients in the retention layer are selected such that the length expands from about 35% to about 60% in the medium within about 2 hours and the width of the retention layer expands from about 30% to about 50% in the medium within about 8 hours.

20. A method of treating a disease in a subject, comprising administering to the subject the dosage form of claim 1, wherein the disease is selected from the group consisting of psoriasis, ankylosing spondylitis, Behcet's disease, rheumatoid arthritis, atopic dermatitis, Crohn's disease, and ulcerative colitis.

21. The method of claim 20, wherein the dosage form is administered once daily.

22. A method of providing in a subject an area under curve (AUC) of a first therapeutic agent ranging from about 70% to about 125% of the AUC of the first therapeutic agent administered BID as an immediate release formulation, comprising administering to the subject once a day the dosage form of claim 1, wherein the amount of the first therapeutic agent in the dosage form ranges from about 60% to about 150% of the daily total amount of the first therapeutic agent in the immediate release formulation.

23. The method of claim 22, wherein the dosage form is administered with food.

24. The dosage form of claim 1, wherein the API layer comprises an intra-granular portion and an extra-granular portion, wherein the intra-granular portion is coated with the extra-granular portion, wherein the Apremilast is disposed in the intra-granular portion only.

25. The dosage form of claim 1, wherein the one or more extended release agents in the API layer comprise a second hypromellose and glyceryl behenate in a ratio ranging from about 1:2 to about 2:1.

26. The dosage form of claim 1, wherein the retention layer further comprises lactose.

27. The method of claim 20, wherein the first therapeutic agent is Apremilast, and wherein when administered QD with food, the dosage form provides an area under curve (AUC) of the first therapeutic agent ranging from about 80% to about 125% of the AUC of the first therapeutic agent in same daily dosage administered twice a day (BID) as an immediate release formulation.

* * * * *